US011602281B2

(12) United States Patent
Bozkurt

(10) Patent No.: US 11,602,281 B2
(45) Date of Patent: Mar. 14, 2023

(54) INJECTABLE SENSORS AND METHODS OF USE

(71) Applicant: North Carolina State University, Raleigh, NC (US)

(72) Inventor: Alper Bozkurt, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 451 days.

(21) Appl. No.: 15/341,756

(22) Filed: Nov. 2, 2016

(65) Prior Publication Data

US 2017/0127975 A1    May 11, 2017

Related U.S. Application Data

(60) Provisional application No. 62/249,626, filed on Nov. 2, 2015.

(51) Int. Cl.
*A61B 5/07* (2006.01)
*A01K 29/00* (2006.01)
(Continued)

(52) U.S. Cl.
CPC ............ *A61B 5/076* (2013.01); *A01K 11/006* (2013.01); *A01K 29/005* (2013.01);
(Continued)

(58) Field of Classification Search
CPC ... A61B 5/0059; A61B 5/0261; A61B 5/0095; A61B 5/0097; A61B 5/076;
(Continued)

(56) References Cited

U.S. PATENT DOCUMENTS 8,175,668 B1 *  5/2012  Nabutovsky ....... A61B 5/14552
                                                   600/323
8,684,925 B2    4/2014  Manicka et al.
(Continued)

FOREIGN PATENT DOCUMENTS

WO    WO 2008036460 A1    3/2008
WO    WO 2011048206 A1    4/2011

OTHER PUBLICATIONS

Ayers, et al., "Fabrication and characterization of silicone-based tissue phantoms with tunable optical properties in the visible and near infrared domain," in Biomedical Optics (BiOS) 2008. International Society for Optics and Photonics, 2008, vol. 6870, pp. 687007-1-687007-9.
(Continued)

*Primary Examiner* — Tammie K Marlen
(74) *Attorney, Agent, or Firm* — Thomas|Horstemeyer, LLP

(57) ABSTRACT

Injectable biophotonic sensors, systems relating to biophotonic sensors, and methods of using the injectable biophotonic sensors and systems are described. Methods and devices for delivering injectable biophotonic sensors to a subject are described. In an embodiment, an injectable biophotonic sensor comprises a printed circuit board (PCB); a light source; a first sensing element; a second sensing element; a receiver device or a induction coil; and an outer casing, wherein the first sensing element, the second sensing element, and the receiver device or the receiver induction coil are coupled to the PCB.

27 Claims, 25 Drawing Sheets

(51) Int. Cl.

| | | |
|---|---|---|
| *A01K 11/00* | (2006.01) | |
| *A61B 5/00* | (2006.01) | |
| *A61B 5/0205* | (2006.01) | |
| *A61B 5/145* | (2006.01) | |
| *A61B 5/1459* | (2006.01) | |
| *A61B 5/318* | (2021.01) | |
| *A61B 5/369* | (2021.01) | |
| *A61B 5/389* | (2021.01) | |
| *A61B 5/398* | (2021.01) | |

(52) U.S. Cl.
CPC ........ *A61B 5/0031* (2013.01); *A61B 5/02055* (2013.01); *A61B 5/1459* (2013.01); *A61B 5/14532* (2013.01); *A61B 5/14539* (2013.01); *A61B 5/14546* (2013.01); *A61B 5/318* (2021.01); *A61B 5/369* (2021.01); *A61B 5/389* (2021.01); *A61B 5/398* (2021.01); *A61B 2503/40* (2013.01); *A61B 2562/0219* (2013.01)

(58) Field of Classification Search
CPC ... A61B 5/0031; A61B 5/1459; A61B 5/1455; A61B 5/02055; A61B 5/0402; A61B 5/0476; A61B 5/0488; A61B 5/0496; A61B 5/14532; A61B 5/14539; A61B 5/14546; A61B 2503/40; A61B 2562/0219; A61B 5/398; A61B 5/369; A61B 5/318; A61B 5/389; A01K 11/006; A01K 11/007; A01K 29/005
See application file for complete search history.

(56) References Cited

U.S. PATENT DOCUMENTS

| | | | | |
|---|---|---|---|---|
| 2002/0026108 A1* | 2/2002 | Colvin, Jr. | ............ | A61B 5/0031 600/316 |
| 2009/0163968 A1* | 6/2009 | Donofrio | ............ | A61B 5/14556 607/6 |
| 2013/0211213 A1* | 8/2013 | DeHennis | ............ | A61B 5/0031 600/316 |
| 2014/0187878 A1* | 7/2014 | Emken | ............... | A61B 5/14532 600/365 |

OTHER PUBLICATIONS

IEEE Standard for Safety Levels with Respect to Human Exposure to Radio Frequency Electromagnetic Fields, 3 kHz to 300 GHz—Amendment 1: Specifies Ceiling Limits for Induced and Contact Current, Clarifies Distinctions between Localized Exposure and Spatial Peak Power Density, IEEE Std C95.1a-2010 (Amendment to IEEE Std C95.1-2005), pp. 1-19, Mar. 2010.
Cheung, K. C. (2007). Implantable microscale neural interfaces. Biomedical microdevices, 9(6), 923-938.
Lee, et al., (2004). Polyimide-based intracortical neural implant with improved structural stiffness. Journal of Micromechanics and Microengineering, 14(1), 32-37.
Hukins, et al., (2008). Accelerated aging for testing polymeric biomaterials and medical devices. Medical engineering & physics, 30(10), 1270-1274.
Ware, et al., (2012). Fabrication of responsive, softening neural interfaces. Advanced Functional Materials, 22(16), 3470-3479.
Ware, et al., (2013). Smart Polymers for Neural Interfaces. Polymer Reviews, 53(1), 108-129.
Gilgunn, et al., (2012). An ultra-compliant, scalable neural probe with molded biodissolvable delivery vehicle. In IEEE 25th International Conference on Micro Electro Mechanical Systems (MEMS), 2012, 56-59.
Brockway, K. A. (2002). Database Support for Microchip Identification in Companion Animal Identification (Doctoral dissertation, University of North Carolina), pp. 1-58.
Zhou, et al., (Aug. 2012). Percutaneously injectable fetal pacemaker: Electrodes, mechanical design and implantation. In Engineering in Medicine and Biology Society (EMBC), 2012 Annual International Conference of the IEEE (pp. 6600-6603), 1-11.
Loeb, et al., (2013). Design and Testing of a Percutaneously Implantable Fetal Pacemaker. Annals of biomedical engineering, 41(1), 17-27.
Sawano, et al., (Jan. 2008). Sealing method of PDMS as elastic material for MEMS. In Micro Electro Mechanical Systems, 2008. MEMS 2008. IEEE 21st International Conference on (pp. 419-422).
Bridges, et al., (2008). Biocompatibility of Implanted Diabetes Devices: Part 2: Anti-Inflammatory Polymeric Coatings for Implantable Biomaterials and Devices. Journal of Diabetes Science and Technology, 2(6), 984-994.
Mercanzini, et al., (2010). Controlled release nanoparticle-embedded coatings reduce the tissue reaction to neuroprostheses. Journal of Controlled Release,145(3), 196-202.
Cameron, et al., 1998. Long-term biocompatibility of a miniature stimulator implanted in feline hind limb muscles. IEEE Trans. Biomed. Eng. 45:1024-35.
Loeb, et al., (2007). Mechanical loading of rigid intramuscular implants. Biomedical microdevices, 9(6), 901-910.
Tan, et al., (2007). Feasibility of prosthetic posture sensing via injectable electronic modules. Neural Systems and Rehabilitation Engineering, IEEE Transactions on, 15(2), 295-309.
Tan, W. (2006). Posture Sensing Techniques for BION (TM) Implants. ProQuest, pp. 1-177.
De Balthasar, et al., (Aug. 2004). Design of antennas to power injectable micro-stimulators: a systematic approach. In 9th Annual Conference of the Inl. FES Society. pp. 839-841.
Hassler, et al., (2010). Characterization of parylene C as an encapsulation material for implanted neural prostheses. Journal of Biomedical Materials Research Part B: Applied Biomaterials, 93(1), 266-274.
Hungar, K., et al., (2008). Gold/tin soldering of flexible silicon chips onto polymer tapes. Journal of Micromechanics and Microengineering, 18(6), 064002, 1-7.
Topper, et al., (Jul. 2006). Biocompatible hybrid flip chip microsystem integration for next generation wireless neural interfaces. In IEEE Electronic Components and Technology Conference, 2006. Proceedings. 56th, 705-708.
Kim, et al., (2008). Electrically small square loop antenna with a capacitive SRR cover structure. In 38th European Microwave Conference. EuMC 2008. pp. 893-896.
Assad, et al., (1999). Comparative in vitro biocompatibility of nickel-titanium, pure nickel, pure titanium, and stainless steel: genotoxicity and atomic absorption evaluation. Bio-medical materials and engineering, 9(1), 1-12.
Davis, et al., (2004). Retrieval of Microstimulators at Human Implant Surgery and Post-Operatively. Proc. 9th Int. Funct. Electr. Stim. Soc, 386-388.
Davis, et al., (2002). Surgical technique to insert and retrieve BIONs (microstimulators) safely near deep nerves for functional electrical stimulation. In J. Proc. 7th Ann Conf Int Funct Electr Stim Soc, Ljubjana, Slovenia (pp. 191-192).
Ziaie, et al., (1996). A hermetic glass-silicon micropackage with high-density on-chip feedthroughs for sensors and actuators. Microelectromechanical Systems, Journal of, 5(3), 166-179.
Alba Medical Systems, Inc. Available online: http://www.albamedical.com/transmitholter.html. (accessed on Jan. 1, 2013), pp. 1-2.
Analog Devices, Inc. Available online: http://www.analog.com/en/mems-sensors/mems-microphones/admp401/products/product.html. (accessed on Jan. 1, 2013), 1-12.
Beerda, et al., J. Mol. Behavioural, saliva cortisol and heart rate responses to different types of stimuli in dogs. Applied Animal Behaviour Science, 58(3):365-381, 1998.
Dog Leggs. Available online: https://www.dogleggs.com/remotemonitoring/. (accessed on Jan. 1, 2013). pp. 1-3.
EMKA Technologies. Available online: http://telemetry.emka.fr/prod.php?prod=4. (accessed on Jan. 1, 2013). pp. 1-3.
Futurlec. Available online: http://www.futurlec.com/Solar Cell.shtml. (accessed on Jan. 1, 2013). pp. 1-11.

(56) References Cited

OTHER PUBLICATIONS

Hiby, et al., Dog training methods: their use, effectiveness and interaction with behaviour and welfare. Animal Welfare-Potters Bar Then Wheathampstead-, 13(1):63-70, 2004.
Sparkfun Electronics. Available online: https://www.sparkfun.com/products/8483. (accessed on Jan. 1, 2013). pp. 1-3.
Sparkfun Electronics. Available online: https://www.sparkfun.com/products/7845. (accessed on Jan. 1, 2013). pp. 1-2.
TSE Systems International Group. Available online: http://www.tse-systems.com/products/implantable-telemetry/animal-telemetry-system.htm. (accessed on Jan. 1, 2013). pp. 1-5.
J. G. Webster, Design of pulse oximeters. CRC Press, 2002, pp. 1-11.
Erhardt, et al., "The use of pulse oximetry in clinical veterinaty anaesthesia," Veterinary Anaesthesia and Analgesia, vol. 17:1, pp. 30-31, 1990.
C. M. Roberts, "Radio frequency identification (RFID)," Computers & Security, vol. 25, No. 1, pp. 18-26, 2006.
Voulodimos, et al., "A complete farm management system based on animal identification using RFID technology," Computers and Electronics in Agriculture, vol. 70, No. 2, pp. 380-388, 2010.
Chawla, et al., "An overview of passive RFID," Communications Magazine, IEEE, vol. 45, No. 9, pp. 11-17, 2007.
Nijland, et al., "Validation of reflectance pulse oximetry: an evaluation of a new sensor in piglets," Journal of Clinical Monitoring, vol. 13, No. 1, pp. 43-49, 1997.
Matthews, et al., "An evaluation of pulse oximeters in dogs, cats and horses," Veterinary Anaesthesia and Analgesia, 30:1, pp. 3-14, 2003.
Bozkurt, et al., "A portable near infrared spectroscopy system for bedside monitoring of newborn brain," Biomedical engineering online, 4:1, pp. 1-11, 2005.
Mendelson, et al., "Noninvasive pulse oximetry utilizing skin reflectance photoplethysmography," Biomedical Engineering, IEEE Transactions on, 35:10, pp. 798-805, 1988.
Mendelson, et al., "Measurement site and photodetector size considerations in optimizing power consumption of a wearable reflectance pulse oximeter," Engineering in Medicine and Biology Society, 2003. Proceedings of the 25th Annual International Conference of the IEEE, vol. 4. IEEE, 2003, pp. 3016-3019.
Strijkstra, et al. (1997). Sleep during arousal episodes as a function of prior torpor duration in hibernating European ground squirrels. J Sleep Res. 6(1):36-43.
Strijkstra, et al., (1997). Ambient temperature during torpor affects NREM sleep EEG during arousal episodes in hibernating European ground squirrels. Neurosci Lett. 221: 177-180.
Walker, et al. (1981). Hibernation at moderate temperatures: a continuation of slow wave sleep. Experientia. 37(7):726-728.
Walker, et al., (1977). Sleep and hibernation in ground squirrels (*Citellus* spp): electrophysiological observations. Am J Physiol. 233:R213-221.
Fee, et al., (2001). Miniature motorized microdrive and commutator system for chronic neural recording in small animals. Journal of neuroscience methods, 112(2), 83-94.
Feng, et al., (2000). A new method for continuous, long-term polysomnographic recording of neonatal rats. Sleep, 23(1), 9-14.
Zielinski, et al., (2013). A novel telemetric system to measure polysomnography biopotentials in freely moving animals. Journal of neuroscience methods, 216(2), 79-86.
Chang, et al., (2011). A novel telemetry system for recording EEG in small animals. Journal of neuroscience methods, 201(1), 106-115.
Grill, et al., (2009). Implanted neural interfaces: biochallenges and engineered solutions. Annual Review of Biomedical Engineering, 11, 1-24.
Wise, et al., (2004). Wireless implantable microsystems: high-density electronic interfaces to the nervous system. Proceedings of the IEEE, 92(1), 76-97.
Hatsopoulos, et al., (2009). The science of neural interface systems. Annual review of neuroscience, 32, 249-266.
Schulman, et al., (2004). Battery powered BION FES network. In 26th Annual International Conference of the IEEE Engineering in Medicine and Biology Society, 2004. EMBC'04. vol. 2, pp. 4283-4286.
Schulman, J. H. (2008). The feasible FES system: Battery powered BION stimulator. Proceedings of the IEEE, 96(7), 1226-1239.
Van Schuylenbergh, et al., (2009). Inductive Powering: Basic Theory and Application to Biomedical Systems. Springer, 1-233.
Lin, J. C. (2003). Safety standards for human exposure to radio frequency radiation and their biological rationale. IEEE Microwave Magazine, 4(4), 22-26.
IEEE Standard for Safety Levels With Respect to Human Exposure to Radio Frequency Electromagnetic Fields, 3 kHz to 300 GHz, IEEE Standard C95.1-1991,1992, pp. 1-250.
Li, et al., (2012). A Wireless Magnetic Resonance Energy Transfer System for Micro Implantable Medical Sensors. Sensors, ISSN 1424-8220, 12(8), 10292-10308.
Malmivuo, et al., (1997). Sensitivity distributions of EEG and MEG measurements. IEEE Transactions on Biomedical Engineering, 44(3), 196-208.
Wendel, et al., (2008). The influence of CSF on EEG sensitivity distributions of multilayered head models. IEEE Transactions on Biomedical Engineering, 55(4), 1454-1456.
Ramon, et al., (2006). Influence of head models on EEG simulations and inverse source localizations. BioMedical Engineering Online, 5(1), 1-13.
Väisänen, et al., (2008). Correlation between signal-to-noise ratios and region of interest sensitivity ratios of bipolar EEG measurements. Medical & Biological Engineering & Computing, 46(4), 381-389.
Väisänen, et al., (2008). New method for analysing sensitivity distributions of electroencephalography measurements. Medical & Biological Engineering & Computing, 46(2), 101-108.
Saager, et al., (2007). Measurement of layer-like hemodynamic trends in scalp and cortex: implications for physiological baseline suppression in functional near-infrared spectroscopy. Journal of Biomedical Optics, 13(3), pp. 1-49.
Young, et al., (2000). Behaviour of near-infrared light in the adult human head: implications for clinical near-infrared spectroscopy. British Journal of Anaesthesia, 84(1), 38-42.
Strangman, et al., (2014). Scalp and skull influence on near infrared photon propagation in the Colin27 brain template. NeuroImage 85, 136-149.
Leonard, et al., (2003). Standard pulse oximeters can be used to monitor respiratory rate. Emergency medicine journal, 20(6), 524-525.
Lee, et al., (2011). Respiratory rate extraction from pulse oximeter and electrocardiographic recordings. Physiological Measurement, 32(11), 1763-1773.
Whitmire, et al., (2013) Kinect-based System for Automated Control of Terrestrial Insect Biobots. 35th International Conference of the IEEE Engineering in Medicine and Biology Society (EMBC'13), Osaka, Japan, 1470-1473.
Harrison, et al., (2007). A low-power integrated circuit for a wireless 100-electrode neural recording system. Solid-State Circuits, IEEE Journal of, 42(1), 123-133.
Harrison, et al., (2009). Wireless neural recording with single low-power integrated circuit. Neural Systems and Rehabilitation Engineering, IEEE Transactions on, 17(4), 322-329, 1-25.
Loeb, et al., (2001). BION™ system for distributed neural prosthetic interfaces. Medical engineering & physics, 23(1), 9-18.
Johansson, A. (2004). Wireless communication with medical implants: antennas and propagation (Doctoral dissertation, Lund University), 174 pages.
Troyk, P. R. (1999). Injectable electronic identification, monitoring, and stimulation systems. Annual review of biomedical engineering, 1(1), 177-209.
Troyk, et al., (2001). Development of BION™ technology for functional electrical stimulation: bidirectional telemetry. In Engineering in Medicine and Biology Society, 2001. Proceedings of the 23rd Annual International Conference of the IEEE, vol. 2, 1317-1320.

(56) References Cited

OTHER PUBLICATIONS

Singh, et al., (2001). Development of BION™ technology for functional electiical stimulation: Hermetic packaging. In Engineering in Medicine and Biology Society, 2001. Proceedings of the 23rd Annual International Conference of the IEEE, vol. 2, pp. 1313-1316.

Jiang, et al., (2010). Technology advances and challenges in hermetic packaging for implantable medical devices. In Implantable Neural Prostheses 2 (pp. 27-61). Springer New York.

Zealear, et al., (2001). The biocompatibility, integrity, and positional stability of an injectable microstimulator for reanimation of the paralyzed larynx. Biomedical Engineering, IEEE Transactions on, 48(8), 890-897.

Lee, et al., "Through-glass copper via using the glass reflow and seedless electroplating processes for wafer-level Rf MEMS packaging," J. Micromechanics Microengineering, vol. 23, No. 8, Aug. 2013, 1-10.

Lee, et al., "Fabrication of void-free copper filled through-glass-via for wafer-level RF MEMS packaging," Electron. Lett., vol. 48, No. 17, Aug. 2012, 1076-1077.

Sun, et al., "The development of low cost Through Glass Via (TGV) interposer using additive method for via filling," in International conference on electronic packaging technology & high density packaging, 2012, pp. 49-51.

Topper, et al., "3-D Thin film interposer based on TGV (Through Glass Vias): an alternative to Si-interposer," in IEEE electronic Components and Technology Conference, 2010, pp. 66-73.

Chang, et al., (2007). Cell and protein compatibility of parylene-C surfaces. Langmuir, 23(23), 11718-11725.

Gruys, et al., (1993). Biocompatibility of glass-encapsulated electronic chips (transponders) used for the identification of pigs. Veterinary Record, 133(16), 385-388.

Clark, A. E. (1974). Solubility and biocompatibility of glass (Doctoral dissertation, University of Florida.), pp. 1-188.

Cui, et al., (2001). Surface modification of neural recording electrodes with conducting polymer/biomolecule blends. Journal of biomedical materials research, 56(2), 261-272.

"FDX-A Microchips." Identipet. n.d. http://www.identipet.com/product/fdx-a-microchips/, Accessed Apr. 5, 2018.

"Injectable Transponder TX1440B10S 12mm Microchip with BioBond Anti-Migration Cap" Identipet. n.d. http://www.dentipet.com:80/fdxb.html, Accessed on Apr. 5, 2018.

"VivoTag RFID Transponder Glass Tubes." SCHOTT North America, Inc. n.d. http://www.us.schott.com/epackaging/english/glass/transponder.html. Accessed on Apr. 5, 2018.

Harrop, et al. "Wearable Technology for Animals 2017-2027: Technologies, Markets, Forecasts." IDTechEx Ltd, http://www.idtechex.com/research/reports/wearable-technology-for-animals-2015-2027-technologies-markets-forecasts-000488.asp. Accessed on Apr. 6, 2018.

Meinhold, Bridgette. "Wearable-Tech Market for Pets Expected to Reawch $2.6 Billion by 2025." Inhabitat, Ecouterre, Jun. 9, 2014, http://www.ecouterre.com/wearable-tech-market-for-pets-expected-to-reach-2-6-billion-by-2025/. Accessed Apr. 6, 2018.

"Cortech Solutions—Small animal EEG." Cortech Solutions, Jan. 26, 2012, http://www.cortechsolutions.com/Applications/Small-animal-EEG.aspx, Accessed Apr. 5, 2018 via WaybackMachine.com.

"Actiwave: a range of ultra miniature waveform recorders for recording ECG, EEG & EMG". Bio-Lynx, 2016, http://www.bio-lynx.com/animal_ecgeegemg.html, Accessed Apr. 5, 2018.

"Piercing Needles—4 Gague, 2", Non-Sterile" Kingpin Tattoo Supply, Jun. 11, 2017, http://kingpintattoosupply.com:80/piercingneedles-4guage2non-sterile.aspx, Accessed Apr. 5, 2018.

"Laser Welding Services—Laserage Technology Coporation." Laserage Technology Corporation, Oct. 25, 2014, http://www.laserage.com:80/welding/, Accessed Apr. 5, 2018 via WaybackMachine.com.

Mauron, Frederic. "Improvements in Glass Encapsulation Technology Offer Significant Advantages for Implantable Medical Devices." Valtronic, Oct. 20, 2016, http://www.valtronic.com/sites/default/files/files/Valtronic%20Glass%20Encapsulation%20White%20Paper.pdf. Accessed Apr. 5, 2018.

\* cited by examiner

INJECTABLE SENSORS AND METHODS OF USE

CROSS-REFERENCE TO RELATED APPLICATIONS

This application claims the benefit of and priority to U.S. Provisional Patent Application No. 62/249,626, filed on Nov. 2, 2015, entitled "INJECTABLE SENSORS AND METHODS OF USE," the contents of which is incorporated by reference herein in its entirety.

STATEMENT REGARDING FEDERALLY SPONSORED RESEARCH OR DEVELOPMENT

This invention was made with government support under grant number 1329738 awarded by the National Science Foundation. The government has certain rights to this invention.

SUMMARY

Provided herein are injectable sensors, which can be injectable biophotonic sensors, having a printed circuit board (PCB), a light source, a first sensing element, a second sensing element, a receiver device or induction coil, and an outer casing, where the PCB, the first sensing element, the second sensing element, and the receiver device or induction coil are coupled to the outer casing. The first sensing element can be a light detector. The second sensing element can be selected from the group of: a temperature sensor, a microphone, an accelerometer, a biopotential electrode, a chemical sensor, a biochemical sensor, a biomolecule sensor, a pH sensor, an ion specific sensor, and any combination thereof. The first sensing element and the second sensing element can each be coupled to the PCB. The first sensing element and the second sensing element can be completely encapsulated by the outer casing. In other embodiments, part of the first sensing element, part of the second sensing element, or parts of both the first sensing element and the second sensing element is integrated with the outer casing such that part of the first sensing element, part of the second sensing element, or parts of both the first sensing element and the second sensing element can be exposed to an environment external to the outer casing. The receiver device or induction coil can be configured to wirelessly couple to a transmitter device or an induction coil. In some embodiments, the transmitter device or induction coil is not coupled to the outer casing. In other embodiments, the receiver device or induction coil and PCB can be completely contained within the outer casing. The injectable biophotonic sensor can further have a transmitter device or induction coil, wherein the transmitter device or induction coil can be coupled to the outer casing. The sensor can further include an electrode, wherein the electrode can be coupled to the PCB board.

Also provided herein are systems having an injectable biophotonic sensor, wherein the injectable biophotonic sensor can have a printed circuit board (PCB), a light source, a first sensing element, a second sensing element, a receiver device or induction coil, a transmitter, where the transmitter is configured to transmit a signal; and an outer casing, where the PCB, sensing element, and receiver device or induction coil are coupled to the outer casing, a receiver, wherein the receiver is configured to receive the signal transmitted by the transmitter, and a transmitter device or induction coil, wherein the transmitter device or induction coil is not coupled to the outer casing, can be external to the outer casing, and is configured to wirelessly couple to the receiver device or induction coil. The transmitter device or induction coil can be coupled to a collar, a bracelet, a vest, a shirt, pants, shoes, a wrap, a brace, or a bandage. The transmitter device or induction coil can be coupled to a structure or planar member. The receiver device or induction coil and transmitter device or induction coil are configured to wirelessly transmit energy from the transmitter device or induction coil to the receiver device or induction coil when the receiver device or induction coil and the transmitter device or induction coil are within responsive proximity to each other. The system can further have a power source, where the power source can be coupled to the transmitter device or induction coil. The system can further have a data storage device, where the data storage device is configured to receive the signal transmitted from the transmitter. The system can further include a processor, where the processor can be in communication with the injectable biophotonic sensor, the data storage device, or both.

Also provided herein are methods that can include the steps of injecting the injectable biophotonic sensor into a subject, wherein the injectable biophotonic sensor comprises, a printed circuit board (PCB), a light source, a first sensing element, a second sensing element, a receiver device or induction coil, and an outer casing, where the PCB, the first sensing element, the second sensing element, and the receiver device or induction coil are coupled to the outer casing. In some embodiments, the methods can further include the comprising the step of detecting a physiologic parameter of the subject by the injectable biophotonic sensor.

BACKGROUND

Remote monitoring of physiological parameters is advantageous in research settings, clinical settings, and wildlife monitoring both in the wild and in captivity. Although such devices exist, they are not without their deficiencies that limit their usefulness in practice. With that said, there exists a need for improved devices for remote monitoring of physiological parameters in a subject.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 2A shows an animal wearing a smart collar, where the animal is also injected with an injectable biophotonic sensor. FIG. 2B shows an enlarged view of the smart collar of FIG. 2A. FIG. 2C shows an embodiment of the injectable biophotonic sensor of FIG. 2A. FIG. 2D shows another embodiment of the smart collar shown in FIG. 2A. FIG. 2E shows the smart collar and system of FIG. 2D in greater detail.

DETAILED DESCRIPTION

Figure 1A:
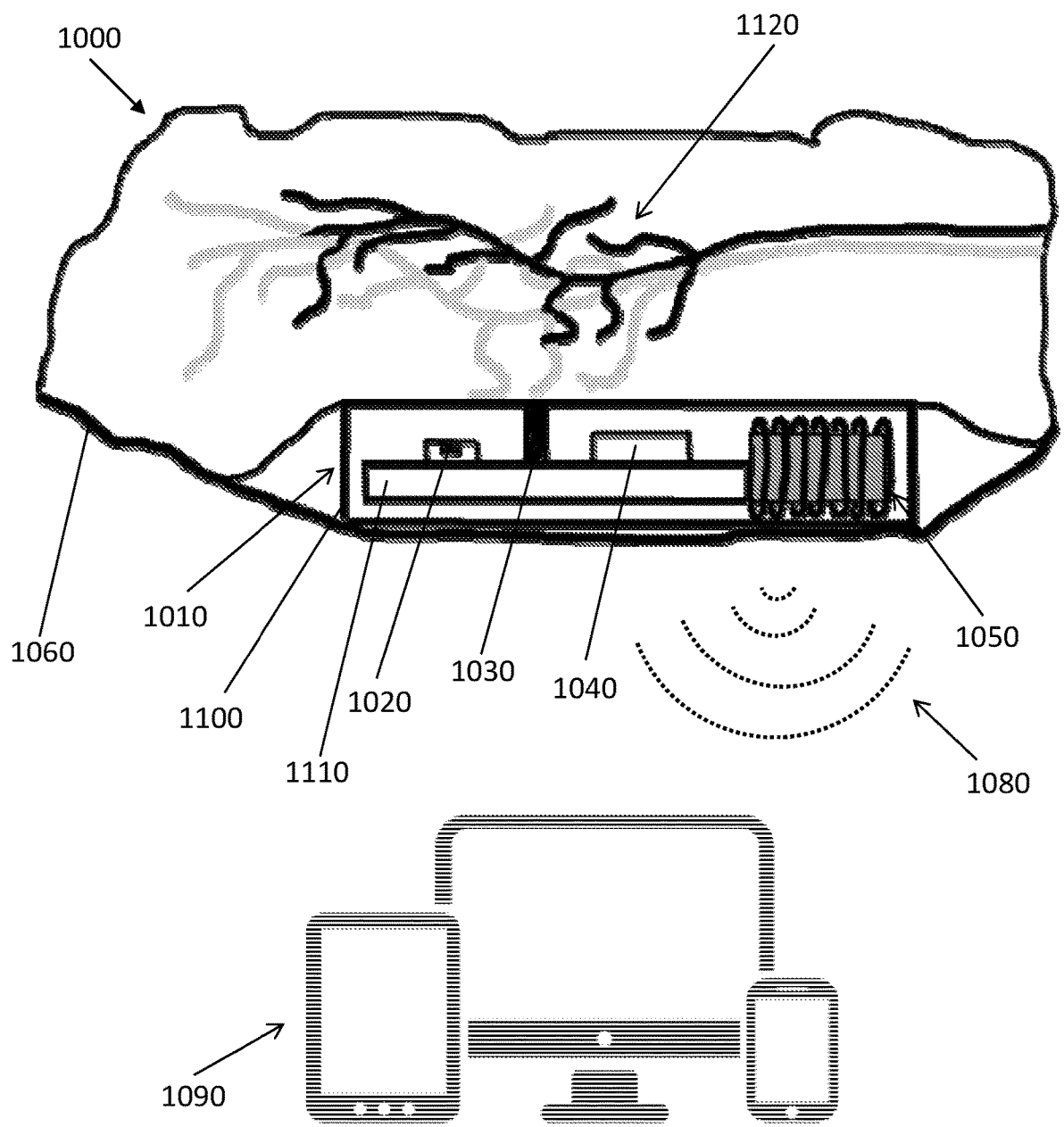
FIGS. 1A-1B show an embodiment of an injectable biophotonic sensor and system without (FIG. 1A) and with (FIG. 1B) an optional material that has optical properties and is sensitive and/or responsive to tissues properties that are on a path of photons emitted from the injectable biophotonic sensor. Measured parameters can include heart rate, heart rate variability, respiratory rate, arterial oxygen saturation, and/or pulse transit/arrival time.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of electrical engineering, computer sciences, biomedical engineering, chemical engineering, physics, mechanical engineering, physiology, biology, medicine, and the like, which are within the skill of the art. Such techniques are explained fully in the literature.

Definitions

As used herein, "wirelessly" refers to any form of communication, energy transmission, data transmission, or signal transmission that occurs without wires between a receiver and transmitter, including but not limited to, optical transmission, sound transmission, magnetic induction, RF transmission, Bluetooth protocol, and WiFi protocol.

As used herein, "responsive proximity" refers to any distance and/or orientation that two objects must be from one another to generate a desired response in one or both objects.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used interchangeably herein, "subject," "individual," or "patient," refers to a vertebrate, preferably a mammal. Mammals include, but are not limited to, murines, simians, humans, farm animals, sport animals, and pets. The term "pet" includes a dog, cat, guinea pig, horse, mouse, rat, rabbit, ferret, and the like. The term farm animal includes, without limitation, a horse, sheep, goat, chicken, pig, cow, donkey, llama, alpaca, turkey, and the like.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a subject.

As used herein, "polymer" can refer to any type of polymer, including but not limited to homopolymers, copolymers, linear polymers, and branched polymers.

As used herein, "homopolymer" can be used to refer to a polymer chain having only one type of monomer.

As used herein, "copolymer" can be used to refer to a polymer chain having two or more different types of monomers within that chain. "Copolymer" can include block copolymers (such as di-block and tri-block copolymers), statistical (random) copolymers, gradient copolymers, and the like.

DISCUSSION

Near infrared based optical sensors have been used extensively in the medical field to noninvasively monitor changes in hemodynamic parameters, such as arterial oxygen saturation as provided by pulse oximetry, blood volume as provided by photoplethysmography (PPG) or local cerebral or muscular oxygen saturation as provided by Near Infrared Spectroscopy (NIRS). Examples of such infrared based optical sensors include fingertip pulse oximeters which are placed over the finger tip of a subject. In animal research and treatment, similar infrared based optical sensors have been used during surgeries by connecting external infrared based optical sensors (such as pulse oximetry clips) on the ear or tongue of anesthetized animals.

Continuous monitoring of multiple parameters on awake and moving animals, particularly wild animals, presents several hurdles to overcome. With respect to external sensors, it can be difficult or impossible to get an animal to tolerate wearing an external sensor device for any amount of time, let alone an extended amount of time that may be required for a long-term monitoring program. Indeed, many animals will simply pull off, bite off, or rub off the device and any tapes, wraps, or other devices used to secure it. Further, external devices often require close or direct contact with the skin to operate. Thus for many devices, hair must be removed prior to use, which may be undesirable. Performance of external sensors can be hindered by the movement of the animal, which may cause the external sensor to move on the skin of the animal. Although tape and wraps can be used to secure the external sensor in place, these must be replaced and repositioned often to avoid irritation to the skin and other side-effects from long term wrapping.

Although implantable devices exist, none can measure multiple physiological parameters and all suffer from limited power which cannot sustain continuous and long-term monitoring and information transmission. As such there exists a need for a non-invasive sensor that can simultaneously measure multiple parameters continuously and for long periods of time, while not requiring surgery to implant the sensor.

With that said, described herein are injectable sensors, which can be injectable biophotonic sensors, and systems that can measure multiple physiologic parameters continuously for extended periods of time that permit noninvasive monitoring of physiologic parameters even in awake and moving animals. These sensors can primarily rely on interaction of light with the tissue to perform a biophotonic assessment and can be augmented by being combined with co-injected biopotential sensors or functional materials. In addition to physiological parameters, the biophotonic signals be used to track activity and/or movement of a subject through motion induced artifacts. The biopotential signals can be fed into adaptive filters as reference signals to reject the motion artifacts in the biophotonic signal, or vice versa. Also described herein are methods of using the injectable sensors and systems. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Injectable Sensors and Systems

Figure 1B:
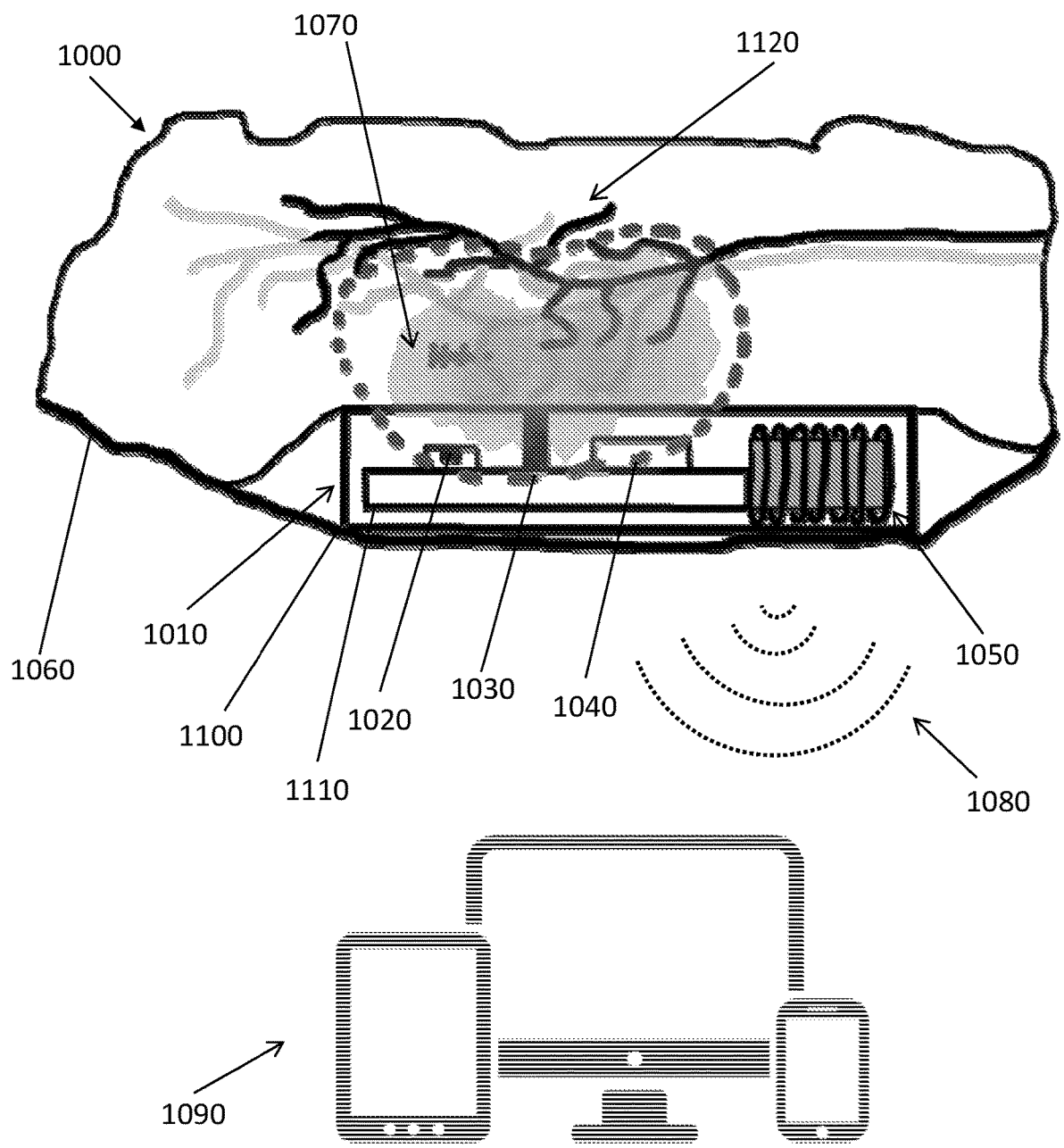

Described herein are injectable sensors, which can be injectable biophotonic sensors, and systems that can be placed subcutaneously in a subject and permit noninvasive monitoring of physiologic parameters even in awake animals. As shown in FIGS. 1A-1B, the injectable biophotonic sensors 1010 of the system 1000 described herein can be placed subcutaneously (under the skin 1060) in a subject. The injectable biophotonic sensor 1010 can contain one or more sensing elements that can be configured to sense (or detect) one or more physiologic parameters or characteristics. Example physiologic parameters or characteristics that can be sensed by the injectable biophotonic sensor include, without limitation, blood flow, blood oxygenation, blood pressure, pulse transit time, pulse arrival time, oxygen saturation, local oxygen consumption, local oxygenation, heart rate, respiratory rate, pH of a physiological fluid or tissue, ion concentration, concentration of a biomolecule or chemical in a tissue or physiological fluid such as glucose, temperature, movement, respiration, brain activity, and muscle activity. In some embodiments, the biophotonic sensors can require co-sensing of bodily sounds or electrical impulses from tissues, organs and/or nerves simultaneously to augment and complement the biophotonic measurements. The injectable sensor can be configured to transmit a signal and/or data to a receiver that is external to the subject. The receiver can be coupled to a data storage device or processor.

As shown in FIGS. 1A-1B, the sensing element can be a light source/detector pair 1020/1040. The light source 1020 (e.g. organic or inorganic light emitting diode (LED)) can be configured to emit light into the surrounding tissue and vasculature 1120. Other suitable light sources can include, but are not limited to, vertical-cavity surface emitting laser, organic and inorganic fluorescent materials and quantum dots. The light emitted from the light source 1020 can interact (e.g. be absorbed and/or reflected) with a tissue of a subject and generate backscattered light that can be detected by the photodiode 1040. The light source 1020 can emit any wavelength of light (or electromagnetic radiation). The electromagnetic wave emitted from the light/radiation source can be any wavelength ranging from about 1 fm (300 ZHz) to about 1 dm (3 GHz). The wavelength can be in the range from ultraviolet (about 10 nm) to IR (about 1 mm) radiation, and be in particular in the visible light range (about 350 nm to about 750 nm) or near infrared (NIR) light range (about 700 nm to about 1200 nm The photodiode output signal can be a current with very low values (for example in the 1-1000 nA range)

In some embodiments where a light source/detector sensing element is used, the injectable biophotonic sensor can further contain a blocker 1030 that can be coupled to the injectable biophotonic sensor such that the blocker reduces the amount of direct light from the light source reaches the photodiode without passing through the tissue. In this way the blocker can inhibit saturation of the photodiode, which can limit the ability of the photodiode to measure backscatter light from the surrounding tissue. Other sensing elements complementing the light source/detector pair include, but are not limited to, a biopotential electrode, temperature sensor, a microphone, a telemetry application-specific integrated circuit, an accelerometer, a chemical sensor, a biochemical sensor, a biomolecule sensor, a pH sensor, a pressure sensor, and an ion specific sensor.

The injectable biophotonic sensor 1010 can be powered by a set of induction coils 1050. The set of induction coils at least contains a receiver induction coil and a transmitter induction coil. The receiver induction coil or both the receiver device or induction coil and the transmitter device or induction coil can be contained in the injectable biophotonic sensor. The receiver induction coil can be configured to wirelessly couple to a transmitter inductive coil when the receiver induction coil and the transmitter induction coil are within responsive proximity to each other. The transmitter induction coil can be external to the subject. The efficiency between the inductor and the transmitter can be enhanced by a magnetic resonance mechanism, such as strongly couple magnetic resonance, by adding extra resonant coils in between. The injectable biophotonic sensors 1010 can include an outer casing 1100 that can contain one or more elements of the injectable biophotonic sensor 1010. On or more components of the injectable biophotonic sensor 1010 can be integrated with and/or coupled to a printed circuit board 1110. The injectable biophotonic sensors 1010 can include a transmitter that can transmit a signal 1080 from the injectable biophotonic sensor 1010 to an external data aggregation or storage device 1090, such as a reader, smartphone, tablet device or a computer, or can be directly uploaded to the internet and/or cloud. The injectable biophotonic sensors 1010 can contain an optional additional or alternative power source.

As shown in FIGS. 1A-1B, one, some, or all of the components of the injectable biophotonic sensor can be contained partially or completely within an outer casing 1100. The outer casing 1100 can be 0% (opaque) to 100% transparent. The outer casing 1100 can be cylindrical, oblong, torpedo, round, egg-shaped, or any other shape. The outer casing 1100 can be longer in one dimension than the other two dimensions. This shape can facilitate injection through a cannula of an injection delivery device. The outer casing can 1100 have a length, a width, and a height. In some embodiments, the outer casing can have a diameter. The length can range from about 1 mm to about 10 cm. The height can range from about 1 mm to about 5 cm. The width can range from about 1 mm to about 5 cm. The diameter can range from about 1 mm to about 5 cm. The outer casing 1100 can be made of a polymer, glass, or other suitable material. The outer casing 1100 can be biocompatible. The outer casing 1100 can also function as a sensor and can be configured to change its properties based on the tissue environment. For example, it can chance absorption, scattering or fluorescence properties based on the pH or glucose level of the interstitial fluid.

As shown in FIG. 1B, in some embodiments, an optically active material that has optical properties can be injected into the subject 1070. In some embodiments this is near the injectable biophotonic sensor 1010. In other embodiments, the material may be injected systemically and thus be circulated to the area near the injectable biophotonic sensor 1010. Electromagnetic radiation from emitted from the light source 1020 can interact with and stimulate the optically active material. In some embodiments, the optically active material is responsive to a tissue characteristic (e.g. pH) that is in the path of the photons emitted from the injectable biophotonic sensor 1010. The photodiode 1040 can then detect light from the optically active material 1070.

Discussion of the injectable biophotonic sensors and systems thereof continue with FIGS. 2A-2E, which shows an embodiment of an injectable biophotonic sensor and system. As shown in FIGS. 2A-B, 2D-2E, the system can include a flexible garment or strap 2010 that can be worn by the subject (e.g. an animal) 2000. The flexible garment or strap 2010 can be, but is not limited to, collar, a harness, a bracelet, a vest, a shirt, pants, shoes, a wrap, a brace, a bandage, or other flexible garment or strap. As shown in greater detail in FIGS. 2B, and 2D-2E, the transmitting device or induction coil 2015, 2030, 2040 can be coupled to or contained within the flexible garment or strap. The flexible garment or strap 2010 can include an transmitter (or transceiver) 2016 configured to transmit a signal 1080 to an external data aggregation or storage device 1090 as described in relation to FIGS. 1A-1B. The flexible garment or strap 2010 can contain one or more sensing elements 2012 and/or actuators 2013. Suitable sensing elements and/or actuators include but are not limited to accelerometers, position sensors, inertial sensors, temperature sensors, barometers, pressure sensors, light sensors, cameras, photodiodes, radioactivity sensors, gas sensors and radio-frequency identification tag readers, a speaker, digital sound source, light sources, speakers, microphone, telemetry system (GPS monitor), transmitter, receiver, a processor, and any combination thereof can be coupled to the flexible garment or strap. The flexible garment or strap 2010 can further contain a power source 2011, such as a battery, or an energy harvesting system based on solar energy or motion of the animal. The power source can be coupled to the transmitter device or induction coil 2015, 2030, 2040, or another sensor, system, or device coupled to the flexible garment or strap 2010. In one embodiment the flexible garment or strap 2010 can also include a telemetry system 2014.

Figure 25:
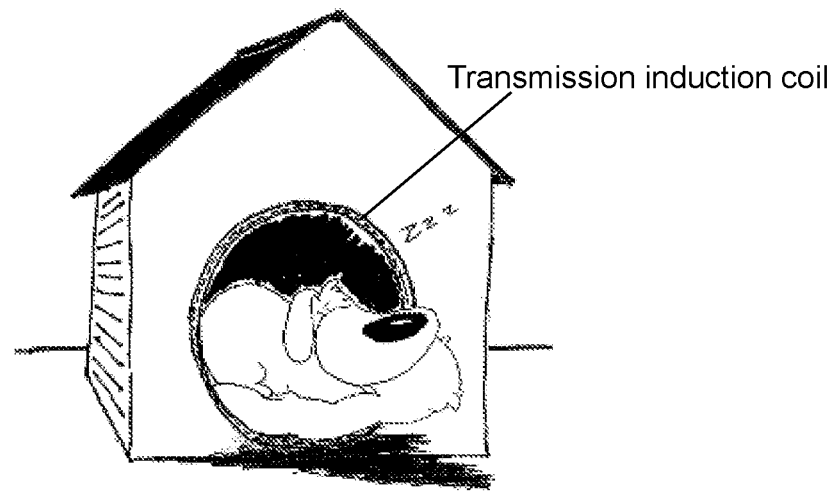
FIG. 25 shows embodiments of a system as described herein where the transmission induction coil can be contained in a structure.
Figure 26:
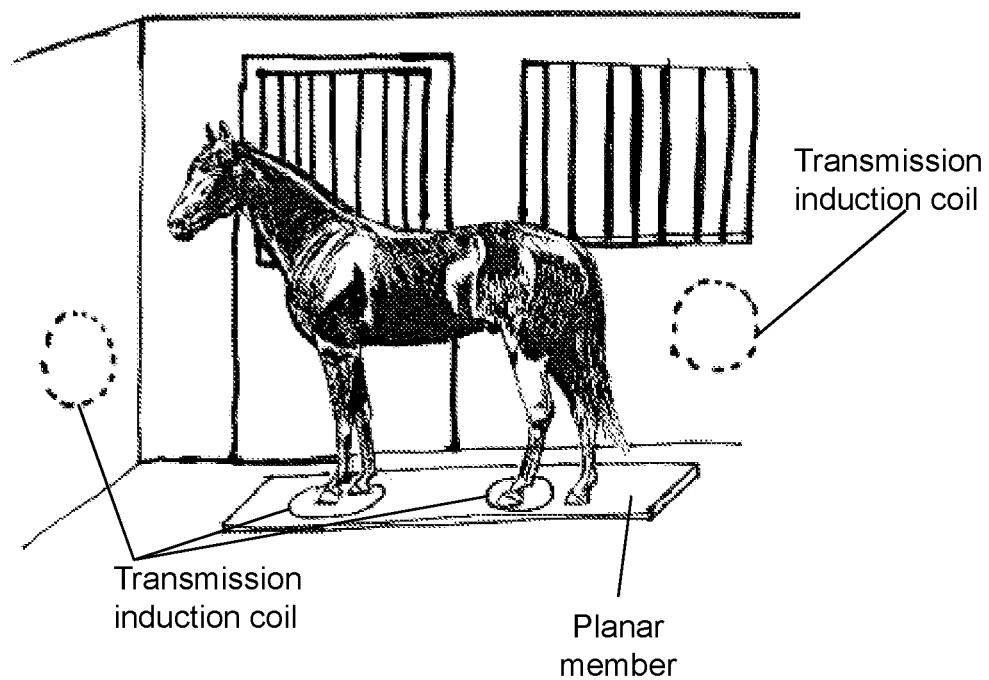
FIG. 26 shows embodiments of a system as described herein where the transmission device or induction coil can be contained in a structure and/or planar member.

As shown in FIGS. 25-26, one or more transmitter inductive coils can be contained in a structure (e.g. a cage, stall, or other enclosure) or planar member. These embodiments afford the advantage that the transmission coil does not have to be worn by the subject. This is advantageous for subjects that will not or cannot tolerate wearing a flexible garment or strap that contains the transmitter device or induction coil. In some embodiments, the structure can be a structure configured to contain the subject, such as a cage, stall, house, bed, rock, box, log, cave, tree, or other structure that can be used by the subject. The transmitter device or induction coil can be coupled to the structure in such a way that the receiver device or induction coil can be wirelessly coupled to the transmitter device or induction coil when the subject is contained in or is in responsive proximity to the receiver device or induction coil. One of skill in the art will appreciate that the orientation of the transmitter device or induction coil in the structure will depend on, among other things, the orientation of the receiver device or induction coil in the injectable biophotonic sensor and the placement of the sensor in the subject. A power source can be coupled to the transmission coil. In some embodiments, the power source can be self-contained (e.g. a battery, super capacitor, or an energy harvesting device). In other embodiments, the power source can be a hard wired electric line.

As shown in FIG. 26, one or more transmitter device or induction coils can be contained in a planar member, such as a mat or a plate that can be placed in/on the floor, a wall, a ceiling of a room, cage, stall, or other structure. A power source can be coupled to the transmission coil. In some embodiments, the power source can be self-contained (e.g. a battery, a super capacitor or energy harvesting device). In other embodiments, the power source can be a hard wired electric line.

In operation, when the subject is in responsive proximity to the transmitter device or induction coil coupled to the structure or planar member, the injectable biophotonic sensor can wirelessly receive energy. This energy can be used or stored for later use by the injectable biophotonic sensor. In a non-limiting example, the structure can be a structure that the subject uses for periods of rest. The transmitter device or induction coil can be positioned within the structure so that when the subject is at rest, the transmitter device or induction coil can be wirelessly coupled to the receiver device or induction coil in the injectable biophotonic sensor that is in the subject. Thus, while the subject is at rest, the injectable biophotonic sensor can receive energy and use the energy and/or store the energy for later use.

Figure 2A:
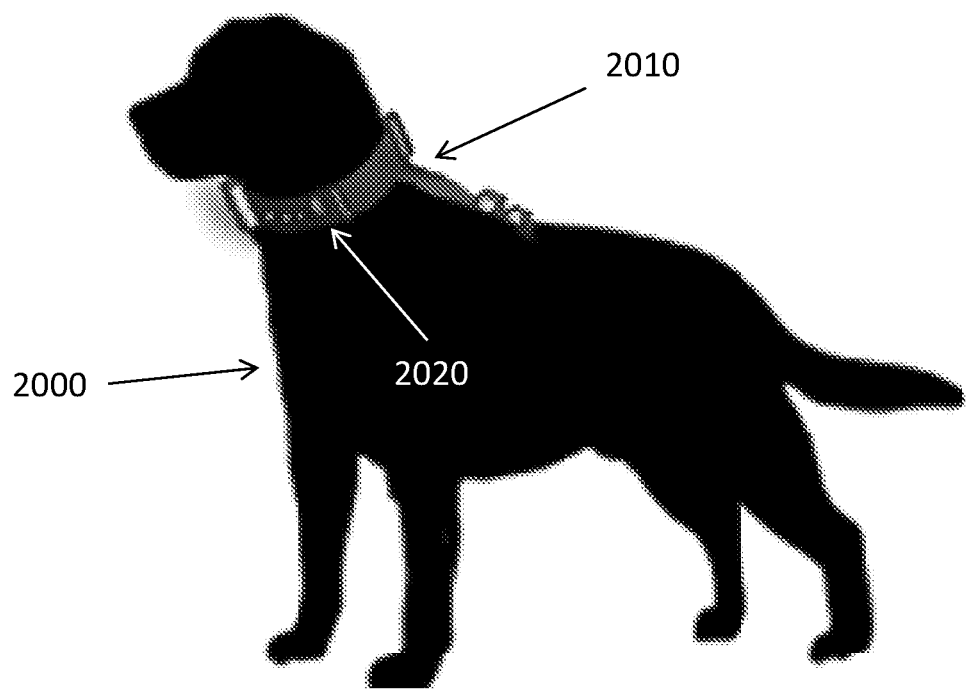
FIGS. 2A-2E shows embodiments of an injectable biophotonic sensor and system.
Figure 2B:
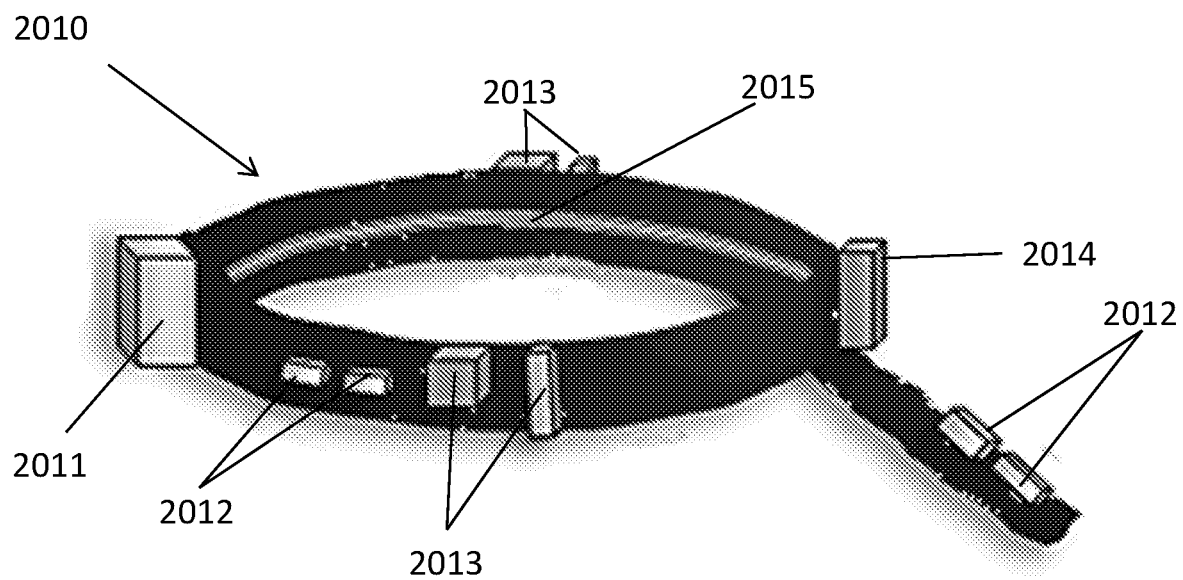
Figure 2C:
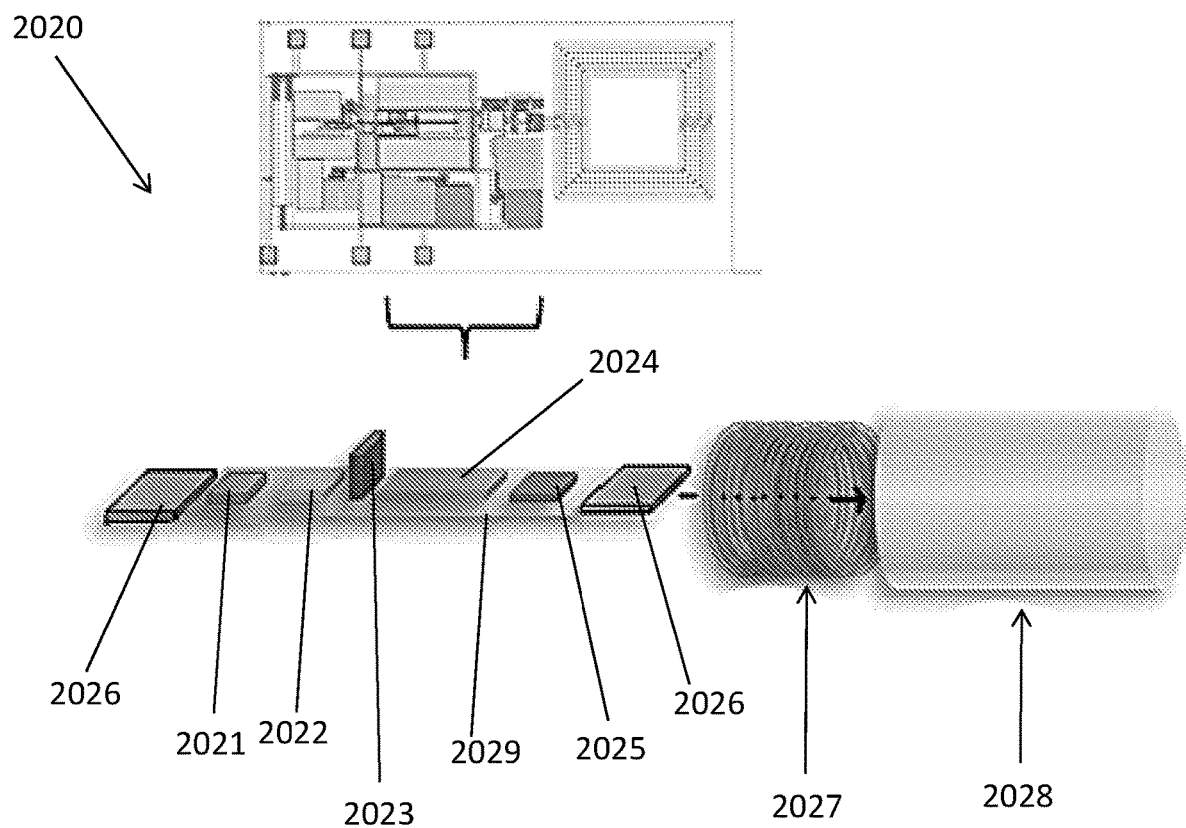
Figure 2D:
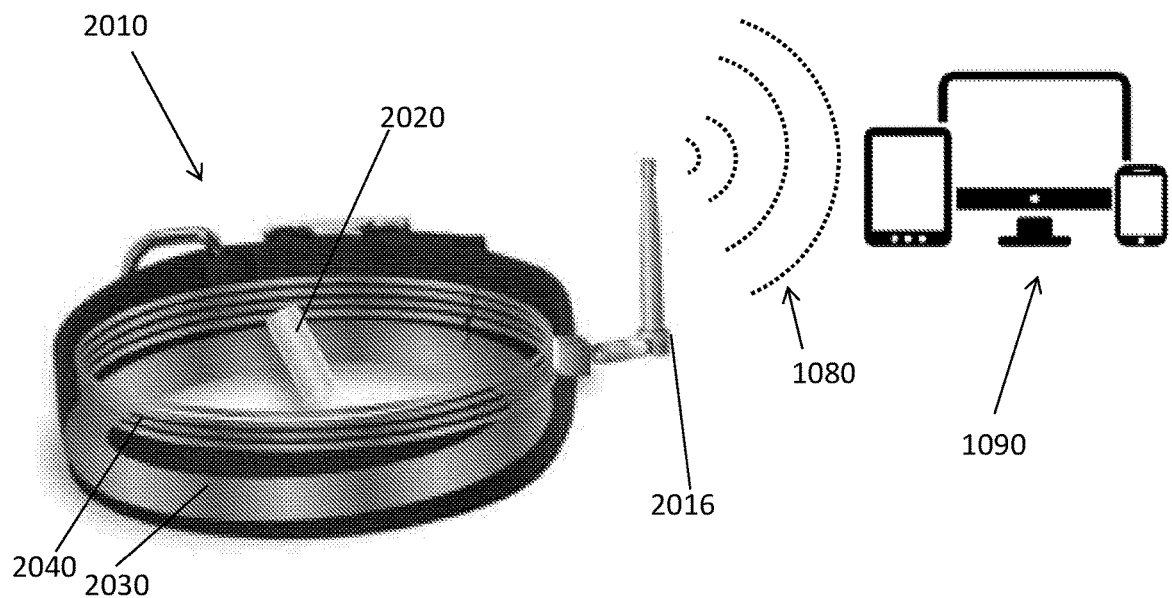
Figure 2E:
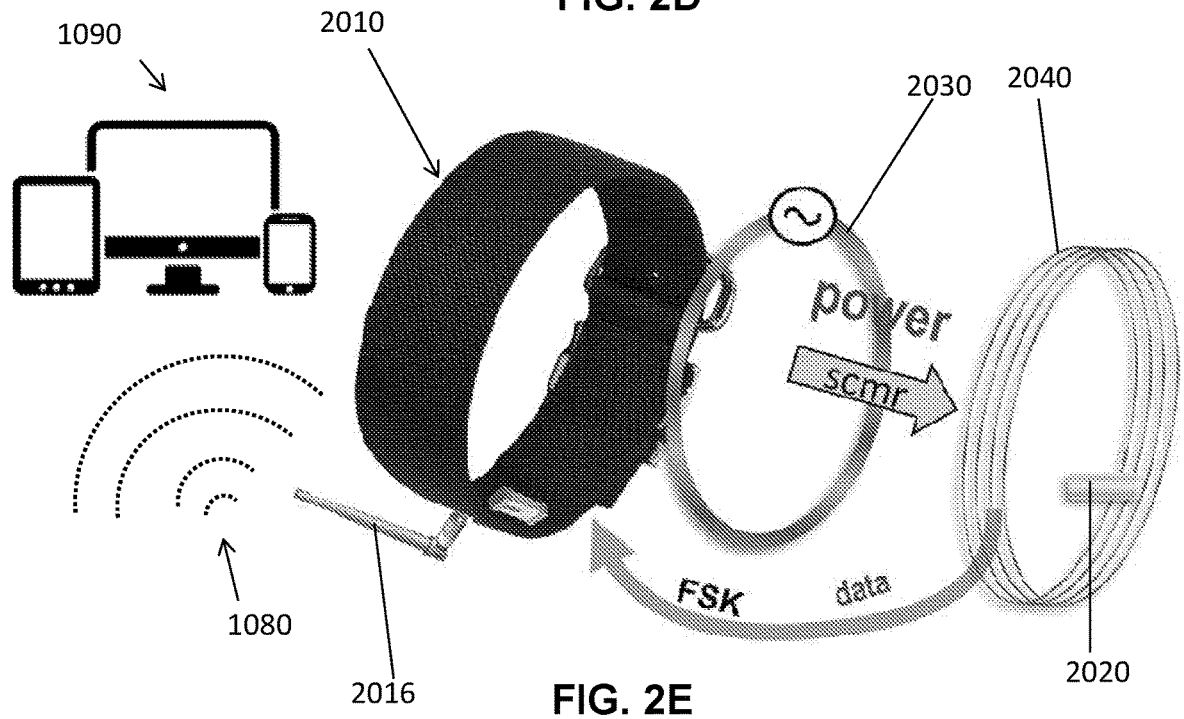

Also shown in FIG. 2C is another embodiment of an injectable biophotonic sensor 2020. The injectable biophotic sensor 2020 can be injected in to a subject in a location near where the subject is going to wear the flexible garment or strap 2010 as shown in FIG. 2A. As shown in FIG. 2C the injectable biophotonic sensor can contain one or more electrical circuits 2024 such as an application-specific integrated circuit that can be coupled to a printed circuit board (PCB) 2029. Other components of the injectable biophotonic sensor 2020, such as a light source (e.g. LED and other suitable light sources as described elsewhere herein) 2021, a photodiode 2025 and other sensing elements 2022 can be coupled to the PCB 2029. The PCB 2029 and other components can be contained within an outer casing 2028 (e.g. a capsule). The PCB and other components can be placed inside the inductive coil 2027 when in the outer casing 2028, such that the at least part of the PCB 2029 can be contained within the void in the center of the receiver device or induction coil 2027.

As shown in FIG. 2C, in some embodiments, the injectable biophotonic sensor can be optionally configured as a biopotential sensor or be also configured as a biopotential sensor. In these embodiments, the injectable biophotonic sensor can include one more electromyography (EMG), electroencephalography (EEG), and/or electrocardiography (ECG), electrooculography (EOG) electrodes 2026. The electrode(s) can be coupled to the PCB 2029. The electrodes can be Teflon insulated wire electrodes.

In some embodiments, the injectable biophotonic sensor can be configured as a biophotonic sensor. In these embodiments, at least one sensing element in the injectable biophotonic sensor is a light source/detector pair. The light source can be and/or light detector can be coupled to the PCB. The injectable biophotonic sensor in these embodiments can also include a blocker as previously described.

In further embodiments, the injectable biophotonic sensor can be configured as both a biophotonic sensor and a biopotential sensor to perform combined experiments. In these embodiments, the injectable biophotonic sensor can have at least one sensing element in the injectable biophotonic sensor is a light source/detector pair and can include can include one more electromyography (EMG), electroencephalography (EEG), and/or electrocardiography (ECG), electrooculography (EOG) electrodes. The electrode(s) can be coupled to the PCB. The electrodes can be, without limitation, Teflon insulated wire electrodes or microfabricated flexible electrode arrays. Other suitable types of electrodes will be appreciated by those of skill in the art in view of this disclosure.

Figure 3:
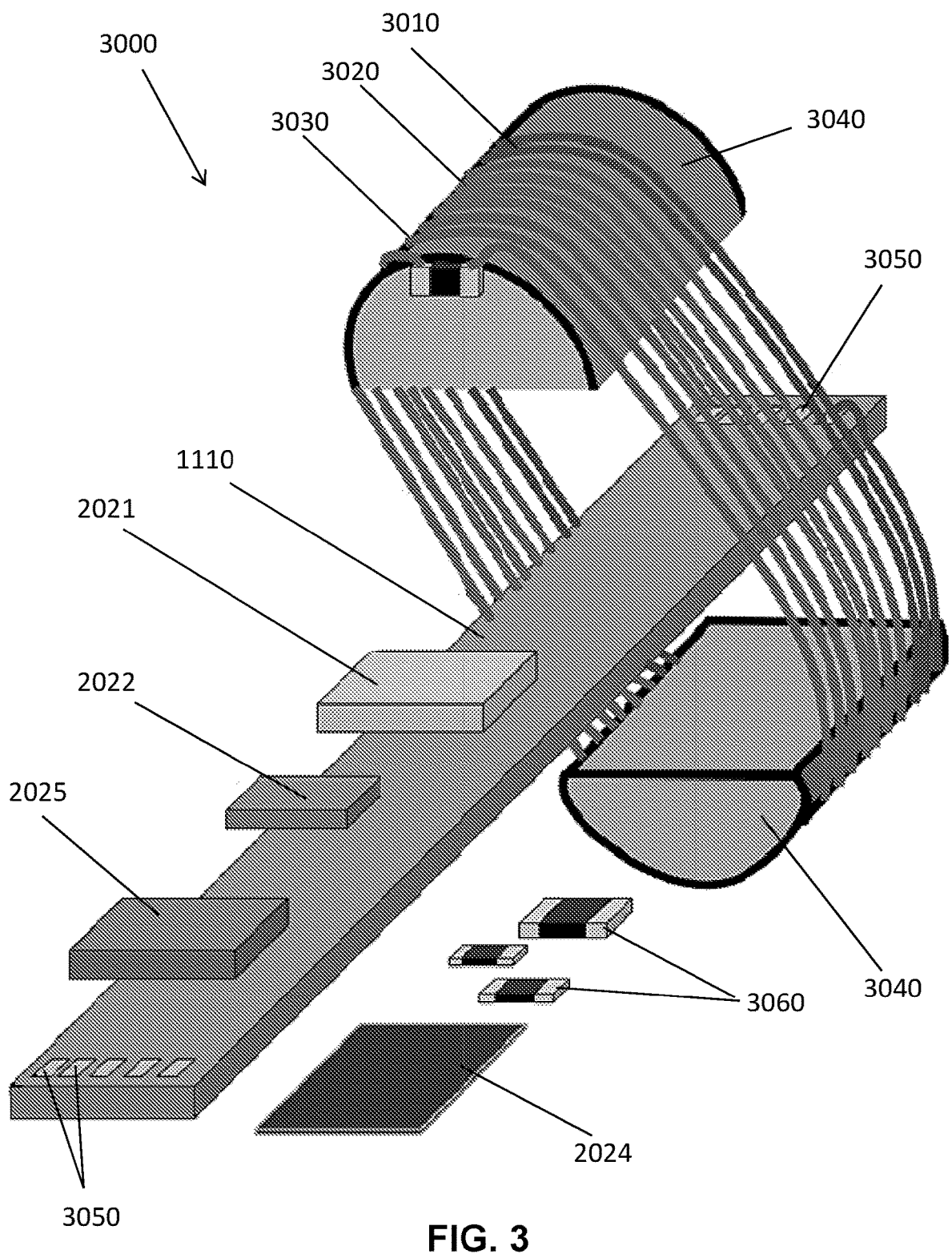
FIG. 3 shows an embodiment of an injectable biophotonic sensor.

Continuing with FIG. 3, in addition to the receiver induction coil 3030, the injectable biophotonic sensor 3000 can include a transmitter antenna coil 3010 and a load coil antenna 3020. The transmitter antenna coil 3010 can be configured to wirelessly couple to and/or wireless communicate with a radio frequency (RF) receiver that is external to the injectable biophotonic sensor 3000. One or more of the aforementioned coils can be wound around one or more pieces of ferromagnetic material. A PCB 1110 can be coupled to the sensing element(s) and other circuits. A light source 2021, photodiode 2025, and any additional sensing elements 2022 can can be coupled to the PCB 1110. Suitable additional sensing elements are described elsewhere herein. Any part of or all of the PCB 1110 and other components can be placed inside the coils, such that the at least part of the PCB 1110 can be contained within the void in the center of the coils. In some embodiments the ferromagnetic material 3040 and/or induction coil(s) can be coupled to the PCB and/or other components of the injectable biophotonic sensor, such as an outer casing (not shown in FIG. 3) and circuitry 2024. In some embodiments, the PCB 1110 can have one or more connection pads 3050. In some embodiments, an electrode can be coupled to a connection pad. As stated previously, the injectable biophotonic sensor can contain circuitry 2024, such as application-specific integrated circuits, that can be coupled to the PCB 1110 or other component of the injectable biophotonic sensor 3000. Wireless transmission can also be through optical transmission, sound transmission, magnetic induction, RF transmission, Bluetooth protocol, or WiFi protocol. Additional external components 3060 can also be included.

Figure 4:
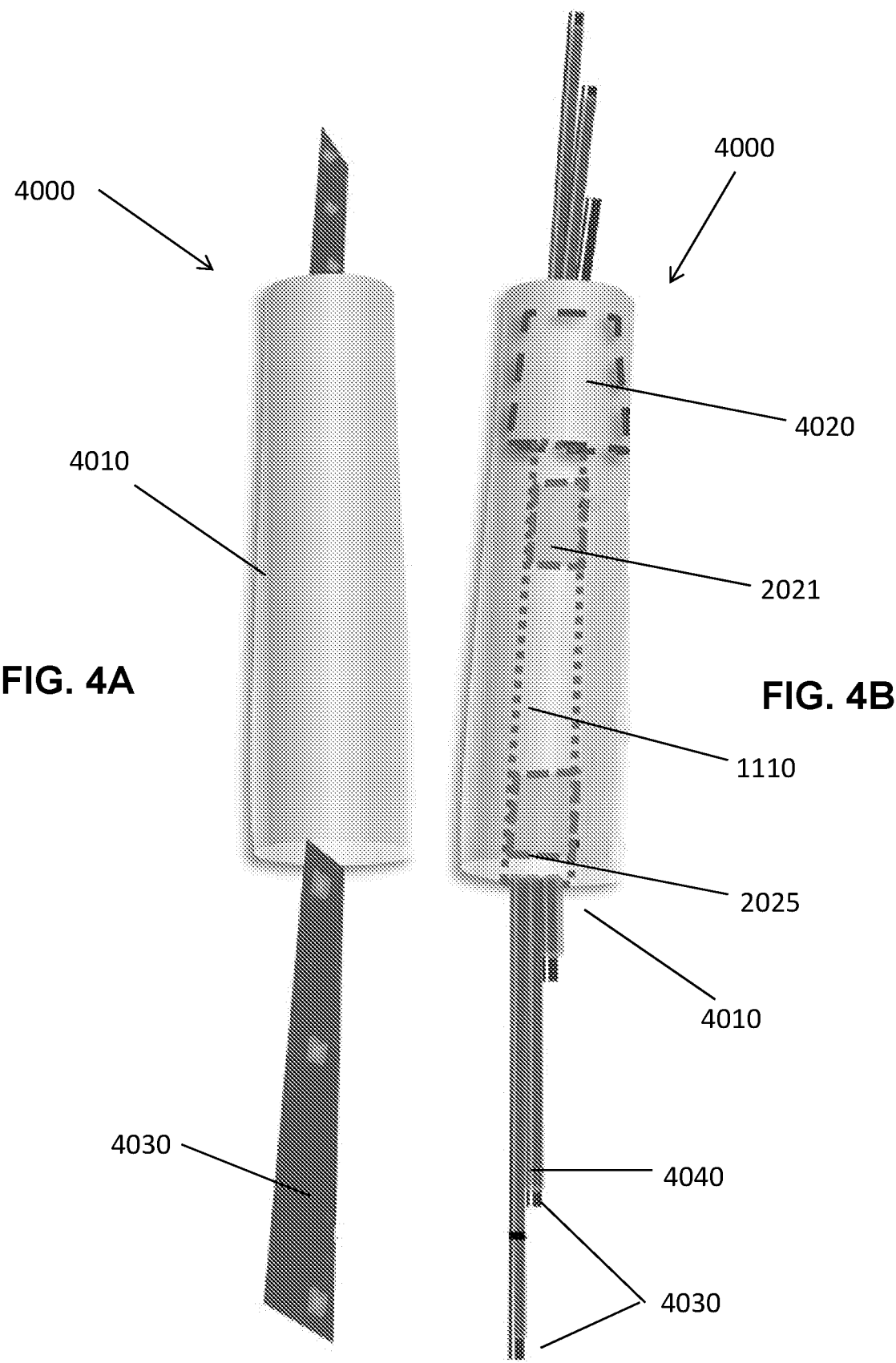
FIGS. 4A-4B show different views of an embodiment of an injectable biophotonic sensor.

Continuing with FIGS. 4A-4B, which shows several views of other embodiments of an injectable biophotonic sensor 4000, the injectable biophotonic sensor can include one or more electrodes 4030 as discussed in relation to, e.g. FIG. 2. The electrodes 4030 can be coated with a polymer (e.g., PEG or other hydrogels) 4040. The polymer can be biocompatible. The outer casing 4010 can be made of glass, a polymer, co-polymer, or a combination thereof as previously described in relation to FIG. 1. In some embodiments, the outer casing 4010 can be covered partially or completely with one or more coating layers. The one or more coating layers can contain one or more polymers. In some embodiments, the polymer can be a Parylene, such as Parylene-C. The outer casing 4010 and/or electrodes 4030 can be coated with one or more pharmaceutical compounds, such as an anti-infective or anti-inflammatory compound. The compounds can be in an extended release dosage form, such as a hydrogel. The outer casing 4010 can house a light source/photodiode pair 2021/2025, which can be coupled to a PCB 1110 and a coil antenna 4020.

Figure 5:
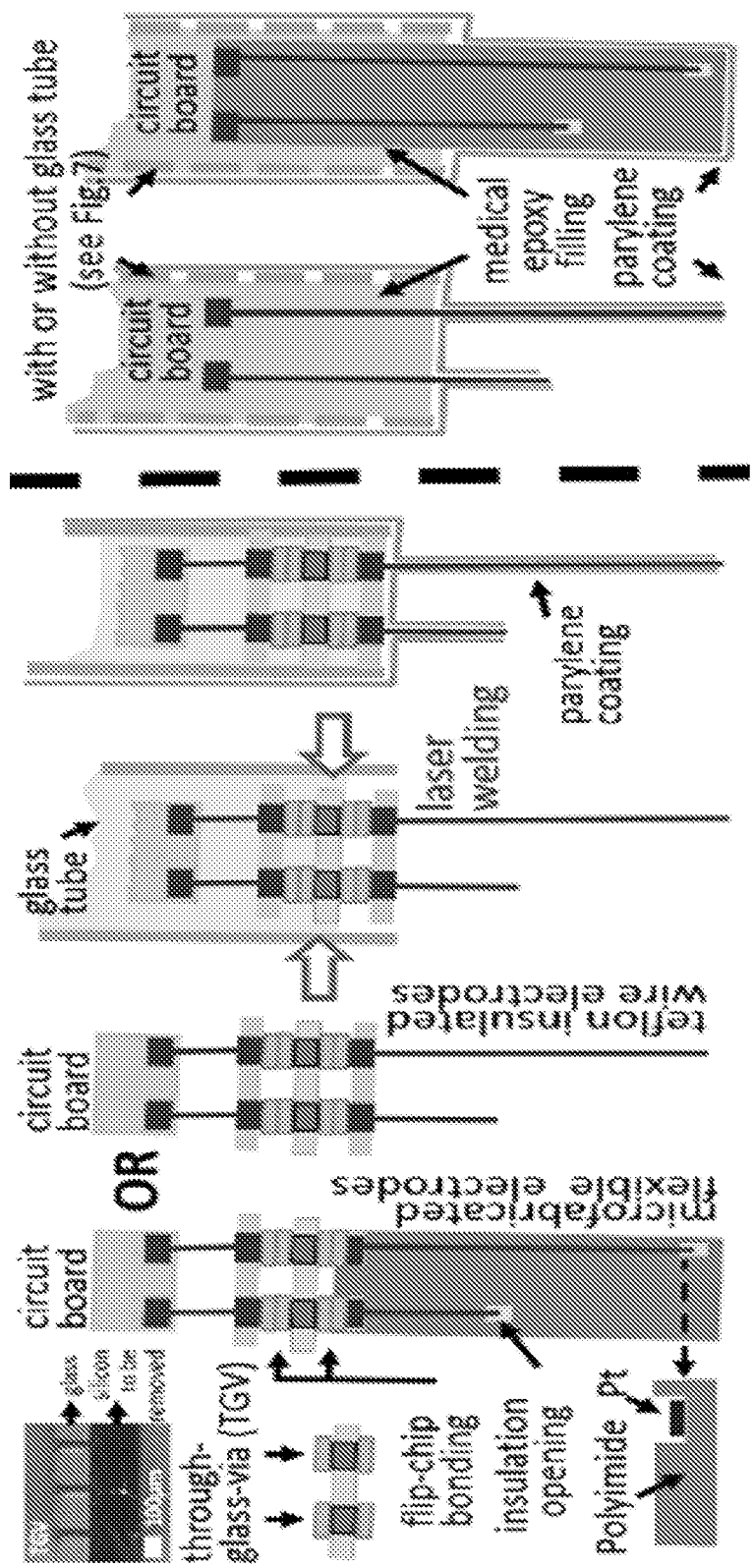
FIG. 5 shows embodiments of an injectable biophotonic sensor.

Discussion of embodiments of injectable biophotonic sensors continues with FIG. 5. As shown in FIG. 5, the injectable biophotonic sensor can contain in some embodiments, microelectronics and micro circuitry. The electrode(s) can be microfabricated flexible electrodes. The microfabricated flexible electrode can contain a flexible member. The flexible member can contain one or more polymers (e.g. polyimide). The flexible member can contain one or more openings. One or more electrode wires can be coupled to the flexible member. The microfabricated flexible electrode(s) can be coupled to the PCB and/or other component(s) of the injectable biophotonic sensor.

As shown in FIG. 5, the outer casing can contain one or more openings through which the electrode (or other component) can be passed through. To prevent exposure of the internal components of the injectable biophotonic sensor to the external environment, the coating layer(s) described in relation to FIGS. 4A-4B, can also cover the electrodes. In this way the internal components and electrodes can be completely sealed off from the external environment.

In some embodiments, voids within the outer casing that exist between the internal components (circuitry, coils, sensing elements, electrodes, and the like) can be filled with an epoxy or other suitable filling. In some embodiments, the filling can be a biocompatible filling. The filling can be a medical grade filling.

Figure 6A:
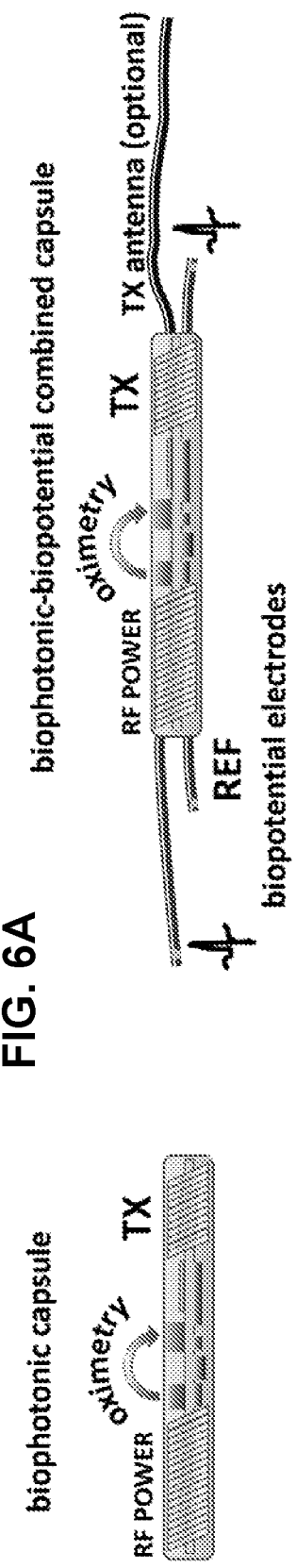
FIGS. 6A-6B shows embodiments of an injectable biophotonic sensor (FIG. 6A) and system (FIG. 6B).
Figure 6B:
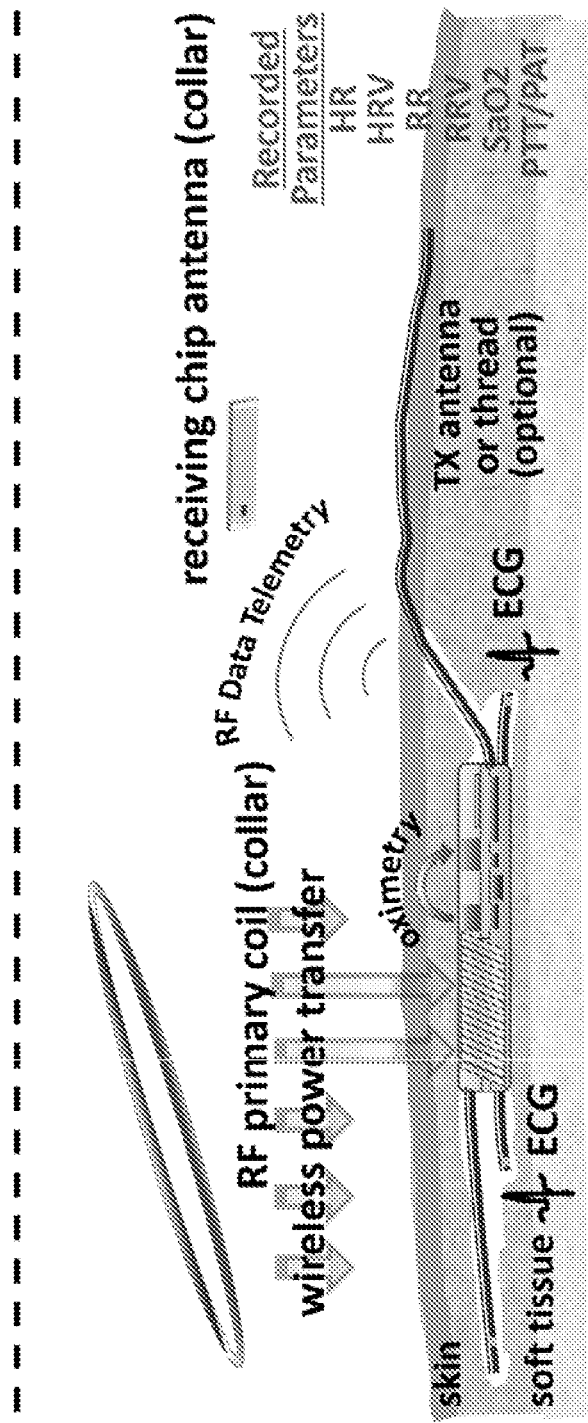

Discussion continues with FIGS. 6A-6B, which shows embodiments of injectable biophotonic sensors, systems, and subcutaneous placement of the sensor in a subject. FIG. 6A demonstrates embodiments of an injectable biophotonic sensor that includes a receiver device or induction coil configured to couple to a transmitter device or induction coil, electrode(s), and a transmission antenna (TX, FIG. 6A) and reference electrode (REF, FIG. 6A). As shown in FIG. 6A, the transmission antenna can extend through the outer casing. The transmission antenna can be coated in a similar fashion to an electrode as described in relation to FIG. 5. As shown in FIG. 6A, the reference electrode can extend through the outer casing. The reference electrode can be coated in a similar fashion to an electrode as described in relation to FIG. 5. As previously described, the injectable biophotonic sensors can contain a plurality of sensing elements. As shown in FIG. 6A, the injectable biophotonic sensor can contain a light source/detector pair, a thermistor (temperature sensor), and one or more electrodes (e.g. EEG electrodes).

As shown in FIG. 6B, the injectable biophotonic sensor can be injected subcutaneously or intramuscularly under the skin of a subject. In some embodiments, a portion of the transmission antenna, reference electrode, and/or other electrodes can remain outside of the subject. The portions of the transmission antenna, reference electrode, and/or other electrodes that are external (outside of the skin layer) to the subject can be secured with one or more sutures, tape, bandage and/or other restraint. The sensing elements and/or electrode(s) can detect physiologic parameters, characteristics, and/or conditions. Data obtained by the injectable biophotonic sensor can be wirelessly transmitted to a receiver via the transmission antenna. As previously described, the injectable biophotonic sensor can be wirelessly powered when the receiver device or induction coil in the injectable biophotonic sensor is in responsive proximity to the transmission device or induction coil.

The injectable sensors, which can be injectable biophotonic sensors, and devices herein can provide advantages to current superficial sensors. They can be placed in a subject to obtain measurements while avoiding artifact creating structures such as the scalp or poor coupling of superficial sensors due to motion artifacts. Furthermore, the subcutaneous measurements that can be achieved by the injectable biophotonic sensors described herein can provide a higher signal-to-noise ratio (SNR) with lower susceptibility to skin artifacts, and less photon absorption/scattering caused by the extra tissue layers between the optical elements placed on skin surface. With respect to oximetry, the injectable sensors, which can be injectable biophotonic sensors, described herein can thus provide more accurate readings that surface based electrodes.

Methods and Devices for Delivering the Injectable Sensors

Figure 7:
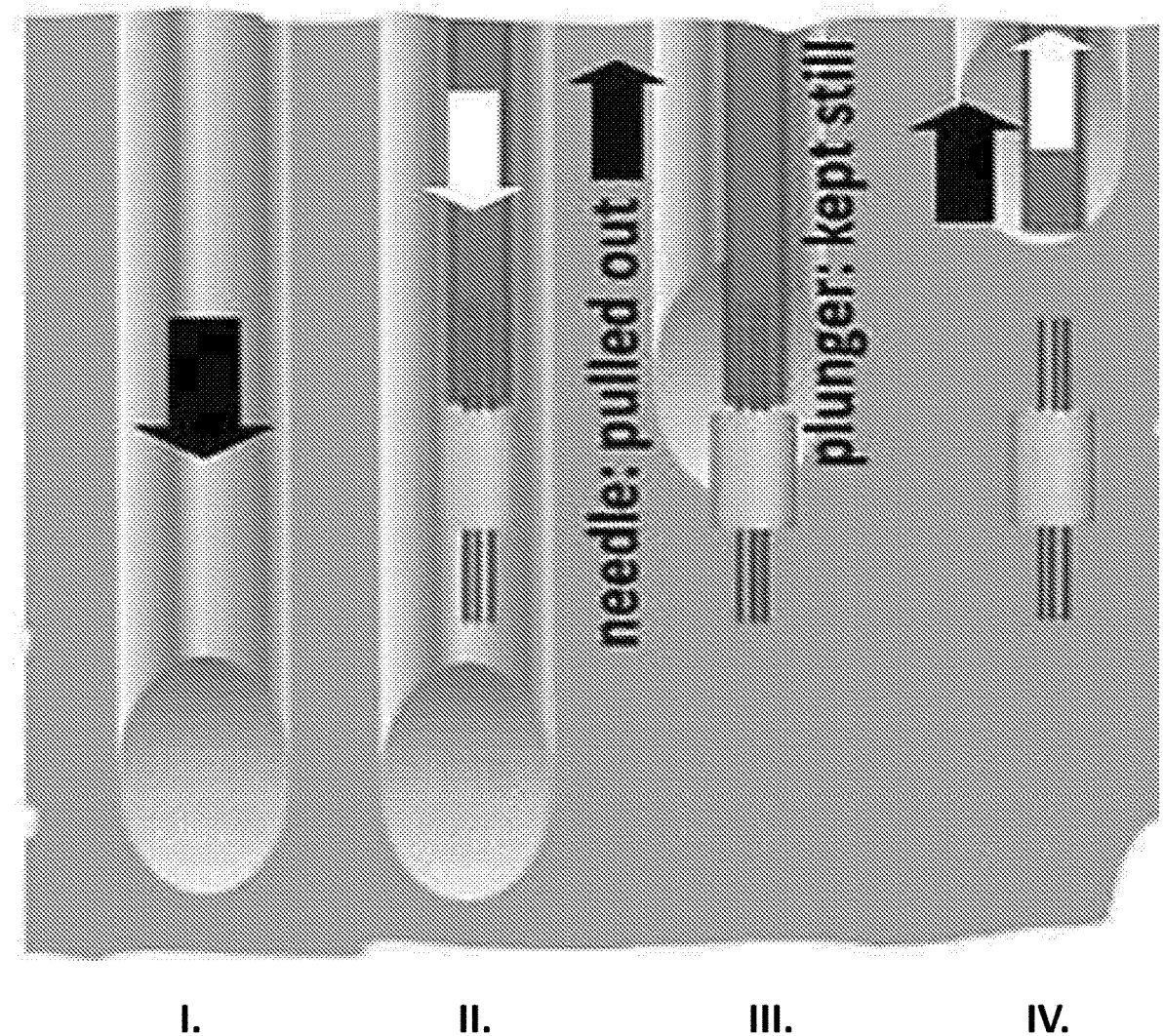
FIG. 7 demonstrates operation of embodiments of an injectable sensor delivery device.

The injectable sensors, which can be injectable biophotonic sensors, described herein can be injected with a delivery device subcutaneously or intramuscularly into a subject. As shown in FIG. 7, the delivery device can contain a cannula. The opening of the cannula at one end can be blunt, tapered, and/or beveled. The cannula can have a cross-sectional shape. In some embodiments, the cross-sectional shape can be round, elliptical, square, rectangular, trapezoid or triangular. The inner diameter of the opening of the cannula can range from about 0.01 cm to about 3 cm.

The delivery device can further contain a plunger. The plunger can push the injectable sensor out of the cannula of the delivery device into the subject. The plunger can be configured to be depressed in response to pressure applied to the delivery device by a user, either directly on the plunger or indirectly through a trigger mechanism on the delivery device.

As shown in FIG. 7, as the plunger is depressed, the injectable sensor can be moved through the cannula of the delivery device, out through the opening of the cannula, and outside of the cannula (e.g. into a subject). As the plunger is released, it moves back through the cannula, leaving the injectable sensor outside of the cannula of the delivery device (and in the subject). The cannula and plunger portions of the delivery device can then be removed from the subject and injection of the injectable sensor can be complete.

Figure 12:
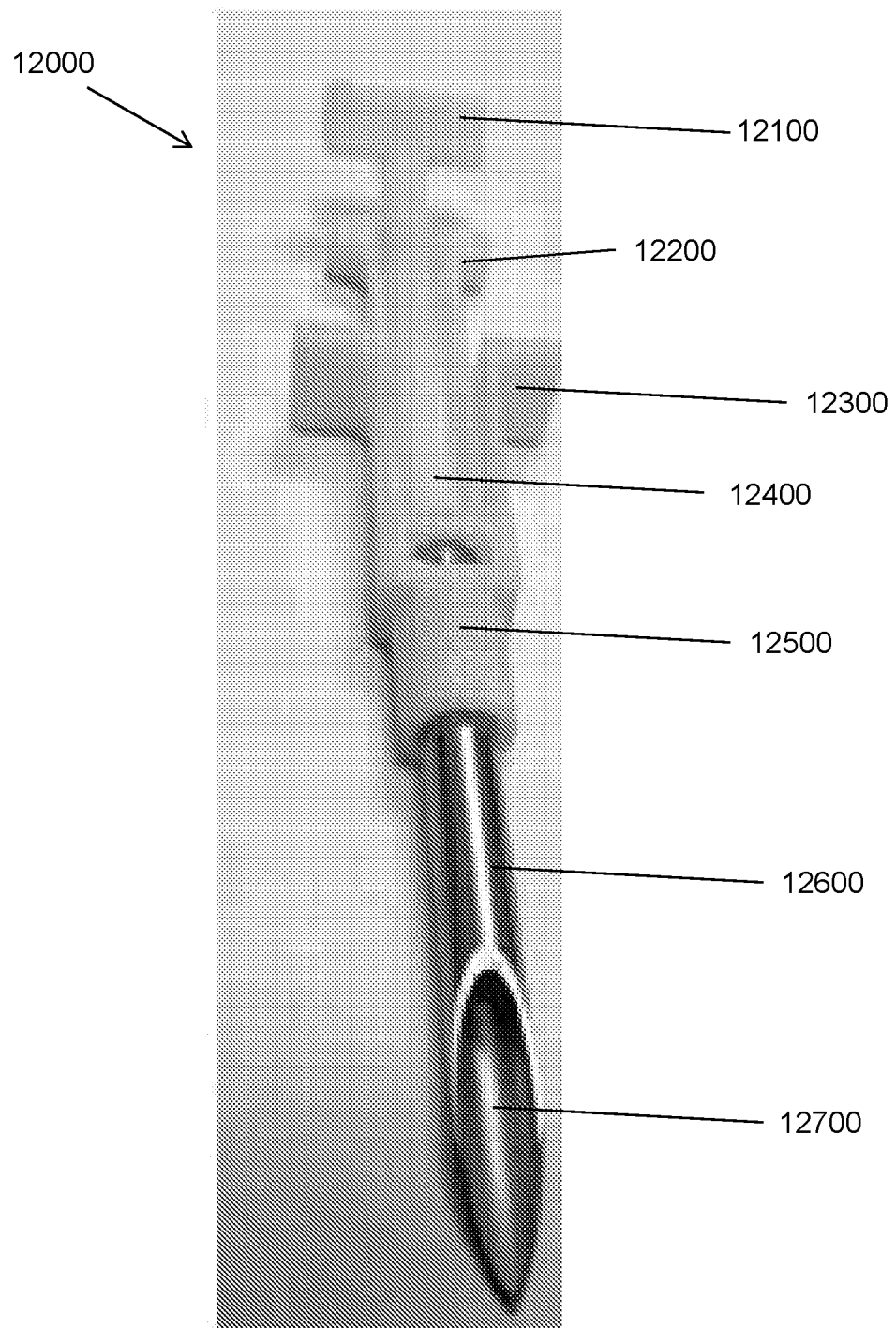
FIG. 12 shows an image demonstrating an embodiment of an injectable sensor delivery device.
Figure 13:
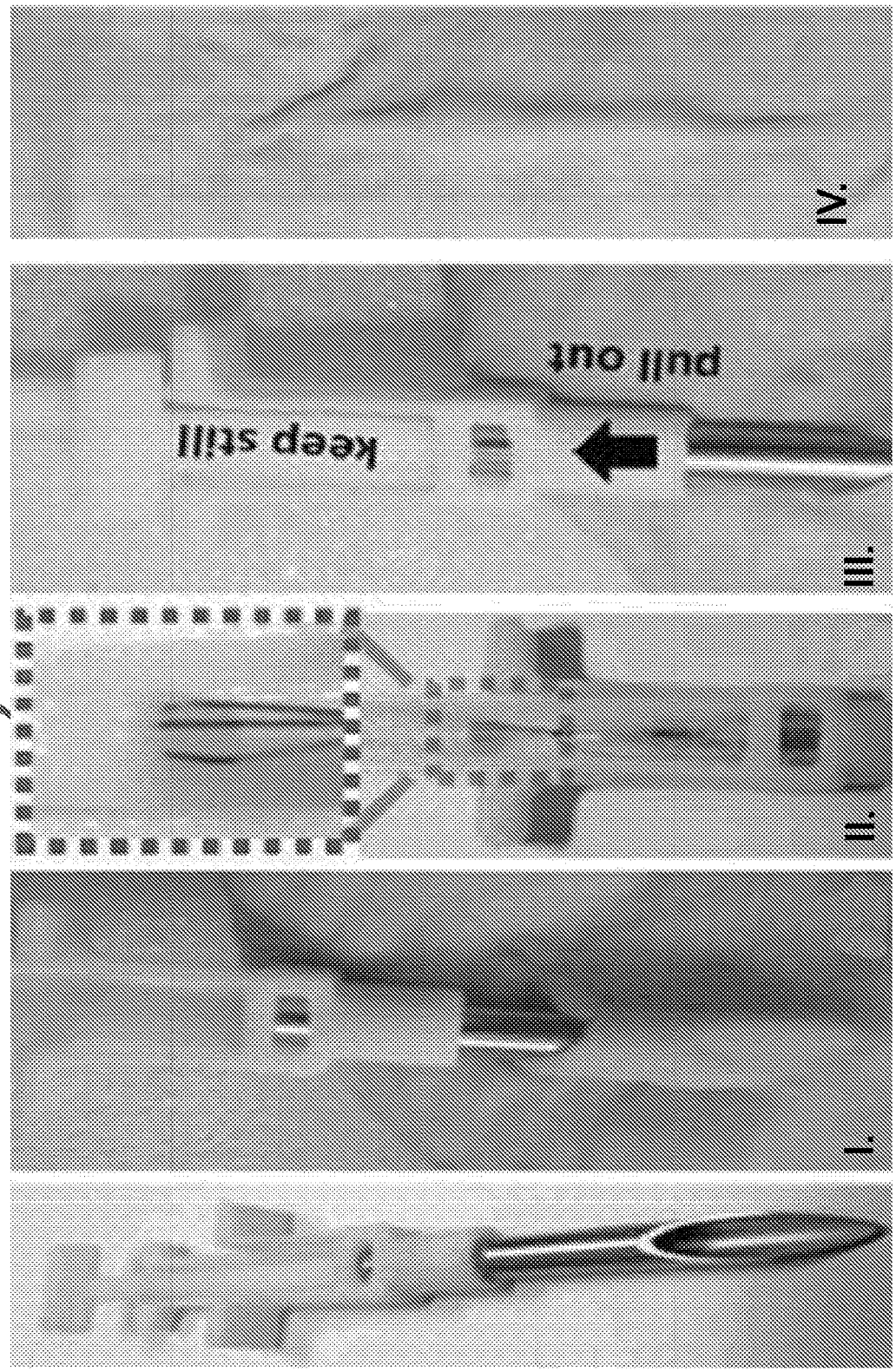
FIGS. 13A-13E shows a series of images demonstrating operation of the injectable sensor delivery device of FIG. 12 and injection of an injectable biophotonic sensor as described herein into a subject.

An embodiment of a suitable delivery device 12000 is demonstrated in FIG. 12. The delivery device 12000 can contain a body portion 12500 and a cannula 12600, where the cannula 12600 can be coupled to the body portion 12500. The body portion 12500 can be configured to receive a cannula 12600 and a plunger 12400. The cannula 12600 can be configured to receive the plunger 12400 through a first opening at one end of the cannula 12600. The plunger 12400 can be configured to slide or slidably move within the cannula 12600. The delivery device 12000 can contain a handle 12100, where the handle 12100 can be integrated with or coupled to the plunger 12400. The body portion 12500 can have one or more grips 12200, 12300, where the one or more grips 12200, 12300 can be integrated with or coupled to the body portion 12500. One end of the cannula 12600, can have a second opening 12700 and this tip can be any desired shape. This tip can be blunt. The tip can be beveled to form a sharp tip that can facilitate injection into a subject. One of ordinary skill in the art will appreciate that gage of the cannula can be varied based on inter alia the exact dimensions of the injectable biophotic sensor, the location of injection, and the subject.

In operation, the user can hold the grip(s) 12200, 12300 of the delivery device 1200 with the hands or fingers. To inject an injectable biophotonic sensor, the user can depress the plunger 12400 by applying pressure to the handle 12100. The plunger 12400 can slide or slidably move within the cannula 12600 and expel an injectable biophotonic sensor that is contained in the cannula out of the second cannula opening 12700. The tip of the cannula 12600

Methods of Using Injectable Sensors

The injectable sensors, which can be injectable biophotonic sensors, and systems described herein can be used to monitor physiologic parameters and other characteristics of a subject. The injectable sensors, which can be injectable biophotonic sensors, and systems described herein can provide continuous detection of physiological parameters and other characteristics of a subject over a period of time. The period of time can range from minutes to years. The injectable sensors, which can be injectable biophotonic sensors, and systems described herein can be used in clinical (including veterinary), research, and/or domestic (home) settings. In some embodiments, the subject is a human. In other embodiments, the subject is an animal. In some embodiments, the animal is a domesticated animal (e.g. dog, horse, cat, mouse, rat, chicken, cow, sheep, etc.) In other embodiments, the animal is a wild animal (e.g. non-human primate, tigers, leopards, elephants, rhinos, bears, wolves, moose, bison, lions, zebra, etc.).

In embodiments, the injectable biophotonic sensors described herein can be injected into a subject and one or more physiological parameters or characteristics can be detected by one or more sensing elements within the injectable biophotonic sensor. A physiological parameter or characteristic of the subject can also be evaluated by analyzing the output of a light detector, which can be part of a biophotonic sensing element, in combination with the output of a secondary sensing element present in the sensor (e.g. temperature sensor, microphone, an accelerometer, a biopotential electrode, a chemical sensor, a biochemical sensor, a biomolecule sensor, a pH sensor, an ion specific sensor, or any combination thereof). In embodiments where the injectable biophotonic sensor or injectable biophotonic sensor system described herein contains a transmitter capable of transmitting data, the transmitter can generate and transmit a signal to a receiver, that can be part of the injectable biophotonic sensor or system thereof as described herein or that can be remote to the subject and/or injectable biophotonic sensor or system thereof. The receiver can be operatively coupled to a data storage device, memory, and/or processor, which in turn, can be operatively coupled to a device (e.g. data storage device, memory, and/or processor) that is part of the cloud network.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

This Example focuses on the case of working animals. Recently, non-invasive and invasive systems for remote monitoring of physiological and emotional states of these animals have been developed in wearable form factors for outdoors setting. No single measure of physiological and emotional monitoring is perfect by itself; therefore, these wearable systems include multiple sensors. Most of the commercially available systems consist of different surface electrodes to record body potentials (e.g., ECG, EMG, and EEG), skin temperature, and strain sensors to measure respiration. Recent Holter systems combines a telemetry system in the form of a jacket or belt worn by dogs. These systems have practical limitations to mitigate stress responses. Animals need to be accustomed to wearing the jacket or belt for two or three days before experiments. The parts of the animals' skin where the electrodes are attached need to be shaved, and the surface electrodes are prone to detachment with the movement of the animal. The skin temperature is also an indirect measurement of the animal's body temperature. Also, most digital Holter devices record data into external memories such as Secure Digital (SD) cards for offline analysis.

Sensors that are superficially attached or fixed on currently available medical vests, and harnesses, and collars can cause discomfort to the animal and can limit the movement of the animal, which can deleteriously reduce the ability of the animal to perform a task (such as search and rescue) or their ability to function normally in their habitat (such as to catch food or care for young in the case of wild animals). Further, setting up the current systems that rely on superficially attached/fixed sensors on animals requires considerable time and effort. Satisfactory skin contact is required for reliable sensing performance, which may be an issue for animals working or living under difficult or harsh environmental conditions.

Other systems have been developed in an attempt avoid this issue by including surgically implantable battery operated sensors to measure core body temperature, biopotentials or other signals. However, these systems are not without limitations. Indeed, to extend the life of the implanted battery, these systems perform measurements every hour or less frequently and are not intended for continuous measurements for chronic applications. Because these sensors require surgery and catheterization for implantation they are useful for medical research, but not for pet, working, or wild animal applications.

Therefore, there is a need for minimally-invasive systems which enable battery-free operation and can remain implanted indefinitely to report physiological data from unrestrained animals. Such systems would enable uninterrupted life time studies similar to "microchip implants". Microchip implants, which are about the size of a large rain of rice, are integrated circuits that use passive RFID (Radio Frequency Identification) technology to identify dogs and other animals (e.g. horses). These are injected under the skin without requiring any anesthesia. Despite their ability to transmit information coded in the microchip device, these devices are unable to measure physiologic characteristics and transmit this information on an ongoing basis and thus have limited use as a relay of information to an outsider about a particular animal by relay of an identification number encoded on on the microchip.

Presented in this Example are at least injectable subdermal capsules in the form factor of microchip implants that can carry physiological sensors (e.g. only biophotonics based sensors and those that combine biophotonics with biopotential sensors) and transponders. The battery-free capsules described here can be powered wirelessly by electromagnetic fields generated by coils that can be embedded in a strap, harness, and/or other garment that can be worn by an animal, such as, but not limited to, a collar around the neck or a vest around the chest. The strap, harness, and/or other garment can contain rechargeable batteries, solar cells or motion-based energy harvesters, COTS microphone chips that can act like a stethoscope to listen to and characterize vocalizations and respiratory patterns of the animal (e.g. such coughing, sniffing, and panting). The strap, harness, and/or other garment can also host sensors (e.g. inertial sensor, motion sensors, and/or accelerometers) to monitor postural and behavioral information.

Near infrared based optical sensors have been used extensively in medical practice to noninvasively monitor changes in hemodynamic parameters such as arterial oxygen saturation as provided by pulse oximetry or blood volume as provided by PPG. In veterinary research, these sensors have been only used during surgeries by connecting pulse oximetry clips on the tongue or ear of anesthetized animals. Continuous monitoring of these parameters on awake and moving animals would help working animal applications and open a new window for medical and veterinary research and clinical practice as well as for the evaluation of working, sporting, and wild animals.

Injectable glass or polymer capsules, similar to microchip implants, would be a form factor overcomes the challenges of wearable monitoring devices which require of hair removal, are prone to detachment and are generally refused by the animals because their mobility is compromised as previously described. The transparent structure of the glass capsules can provide optical transmission of photons in the infrared region of the spectrum to perform reflectance-based oximetry where with the same light-source and detector pair heart rate (HR), respiratory rate (RR) and arterial oxygen saturation ($SaO_2$) can be monitored (FIG. 1). Traditional pulse oximetry devices are physically attached to the skin and require the emission (radiation) of redundant photons to account for undesired absorption in the skin and lipid layers. The light absorption by the tissue requires more photons to be injected, thereby raising the power consumption that in turn increases the conducted heat due to heating of semiconductor junctions inside the light emitting diode (LED) and imposing a safety limit to avoid thermal injure of skin. More power efficient devices can be designed with injectable form factors where the intrinsic attenuation of fur and skin is not present and the signal to noise ratio is potentially higher. Being directly within the tissue also avoids limitations imposed by skin detachment with motion artifacts and the resulting leakage of the ambient light to the sensors.

These capsules and systems presented in this Example can be injected subcutaneously in the animal, such as and without limitation in the neck region right beneath an electronic collar that carries a bidirectional radio for communicating with a remote base station or data aggregator (see FIG. 2). The collar can also host inductive coupling loops to power and communicate with the capsule. The capsule can contain, for example, four groups of elements: (1) sensors, (2) one or more integrated circuit(s) (e.g. an application specific integrated circuit (ASIC), (3) a coil inductor with a ferrite core, and (4) a capacitor. The sensors, either individually or collectively, can be configured to detect one or more physiological parameters or characteristics and provide physiologic data to and/or perform analysis of the physiologic data, such as and without limitation, near-infrared spectroscopy (NIRS), pulse oximetry, and/or photoplethysmogram (PPG). The integrated circuit can contain one or more of any of the following: amplifier(s), oscillator(s), rectifier(s), filter(s), bandgap references, multiplexer(s), analog-to-digital converter(s), resistor(s), and transistor(s). Specific examples of these components and their inclusion in an integrated circuit will be appreciated by one of ordinary skill in the art.

In order for the groups of elements in the capsule to work together, the integrated circuit can be coupled to one or more of external components: a light source to inject photons into the tissue and a photodiode to sense these photons; the receiver coil for inductive coupling to wirelessly power the circuit; the ferrite core around which this coil is wound to increase the magnetic field that passes through the coil, and thereby its quality factor; and, a capacitor that can be connected between the supply and ground. The photodiode output signal can be a current with very low values (for example ranging from about 1-1000 nA). The electromagnetic wave emitted from the light source can be any wavelength ranging from about 1 fm (300 ZHz) to about 1 dm (3 GHz). The wavelength can be in the range from ultraviolet (about 10 nm) to IR (about 1 mm) radiation, and be in particular in the visible light range (about 350 nm to about 750 nm) or near infrared (NIR) light range (about 700 nm to about 1200 nm).

The light can be modulated to minimize the 1/f noise and can be duty cycled to lower the power consumption and eliminate the diode heating. The receiver side of the circuit can include a low noise amplifier, a low bandpass filter, and a mixer to demodulate the frequency modulated light. The amplified, filtered, digitized and multiplexed signal can be frequency-modulated and transmitted using an antenna, which can in some embodiments, be a component of an oscillator contained in the integrated circuit. The modulation can be achieved by one or more varactors (such as without limitation, two accumulation-mode metal-oxide-semiconductor (MOS)) that can also be included in the integrated circuit.

A higher frequency (as compared to the light modulation previously described) inductive coupling link can be used to power the device. The raw signal received by an external coil in the capsule can be fed into a rectifier and filtered by a filter or other suitable device. This supply voltage can drive all the different blocks of the system, including any biasing circuitry that can be included to generate all voltages and currents used for operation of the any components of the integrated circuit. In addition to this powering circuitry, a bandgap reference can be included to create a stable voltage with a low temperature variation. This voltage can be used for stabilizing the output of an amplifier and as the supply voltage the oscillator.

A sensor in the capsule can contain a surface-mount light source (e.g. LED) and photodetector pair configured to perform the basic photoplethysmography functionality. Due to power and size constraints, an ultra-compact and low-power photodetector can be employed. A LED that is enclosed in a thin surface mount package (e.g. 0402) can be used as the light sourceThese two main components can be placed on a PCB. Due to the proximity between the components of the sensor a light blocker made of tinted hard resin can be included to prevent the saturation of the photodetector caused by the direct light of the LED (see FIGS. 1 and 8, 11-12, and 14-15). The conventional reflectance method for performing photoplethysmography is based on having the light source and photodetector facing the same directions but tightly coupled to tissue to avoid direct light transfer between the LED and photodetector. In this configuration, the photodetector collects the backscattered light after passing through the blood vessels contained in the probed tissue.

In order to make the system wireless, a coil for powering the sensor through inductive coupling can be included. The coil can be assembled by winding a magnet wire around a ferrite rod to improve the coupling. The power transmission can be achieved by means of a Zero Voltage Switching (ZVS) Flyback driver using a loop antenna.

Figure 14:
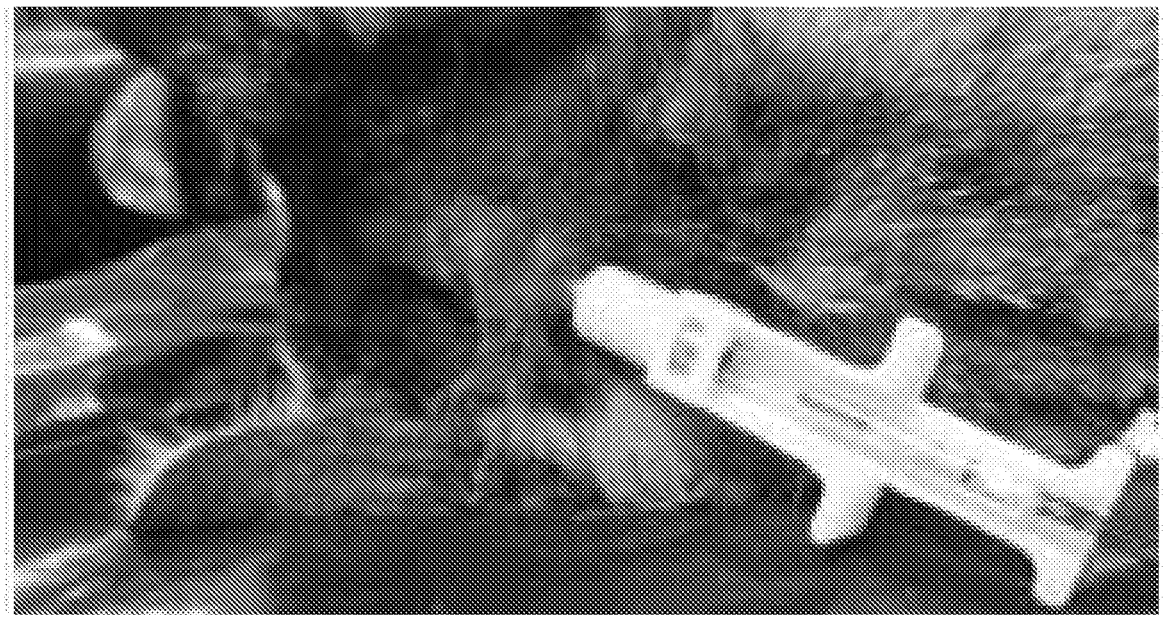
FIG. 14 shows an image demonstrating injection of an injectable biophotonic sensor as described herein into a subject using an injectable sensor delivery device as described herein.
Figure 15:
FIG. 15 shows an image demonstrating an injectable biophotonic sensor as described herein after injection into a subject.

In parallel to the glass tubes, encapsulating the electronics with medical grade epoxy can be another packaging strategy. Both capsules can be designed and configured to withstand the injection procedure and prevent the interaction between electronics and subcutaneous tissues (see FIGS. 8, 11-12, and 14-15). The glass can be sealed at both ends. The epoxy capsule can be fabricated by first preparing a cylinder-shaped hole defined in a silicone block filled with the epoxy material and then pushing the PCB inside the hole to immerse it in the epoxy. After the curing process the silicone mold can be broken open. Finally, a custom injector can be manufactured to accommodate the capsule during the injection procedure by fitting a 3D printed syringe with a larger diameter needle that can accommodate the capsule, as shown in FIG. 12. This injector was tested by introducing one of the capsules between the scalp and the skull of a cat cadaver as shown in FIGS. 12 and 14-15.

Figure 11:
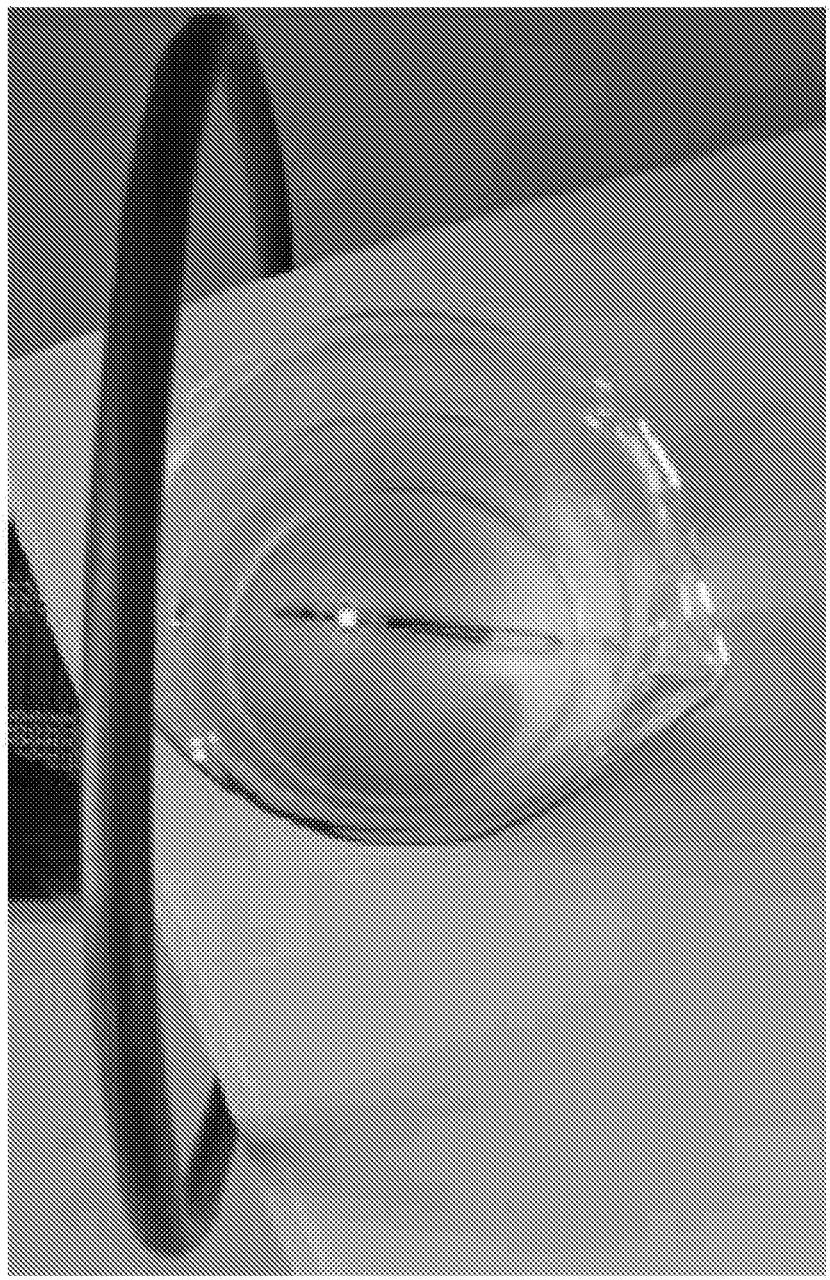
FIG. 11 shows an image demonstrating of an injectable biophotonic sensor and system as described herein.

In order to test the feasibility of inductive power coupling of the sensor, the sealed glass capsules was first located in glass beakers filled with saline solution and powered using a custom transmitter with a built-in ZVS Flyback driver, observing the light output from the red LED (see FIG. 11). For this experiment, a simple PCB design can be used with the LED connected to a regular diode in series to rectify the signal and resulting with an increase in the required forward voltage. The optical light output can allow the power received in the capsule to be estimated without connecting any wires that would eventually act as a coil and cause inaccurate measurements. As discussed below, this test was performed and at least demonstrates the powering of light sources and detectors through wireless inductive coupling. Light emission was visually observed from the LED with an applied power of 250 m W/cm². This caused only 0.2° C. temperature increase during a 5 hour experiment.

For the second experiment, a photodiode was coupled to the PCB for recording the backscattered light when the capsule is inserted into a tissue mimicking phantom. The photodiodes can be accessed by soldered wires to the PCB where one end of the capsule can be sealed with a torch and the other one using medical epoxy (see e.g. FIGS. 8, 10, and 14-15 and 3). Silicone-based optical phantoms in the visible and near infrared ranges were assembled (F. Ayers, A. Grant, D. Kuo, D. J. Cuccia, and A. J. Durkin, "Fabrication and characterization of silicone-based tissue phantoms with tunable optical properties in the visible and near infrared domain," in *Biomedical Optics* (*BIOS*) 2008. International Society for Optics and Photonics, 2008, pp. 687 007-687 007). The core material of these phantoms is vulcanized silicone, to which rutile titanium dioxide powder (to obtain the scattering) and India ink (to tune the absorption) was added.

Figure 18:
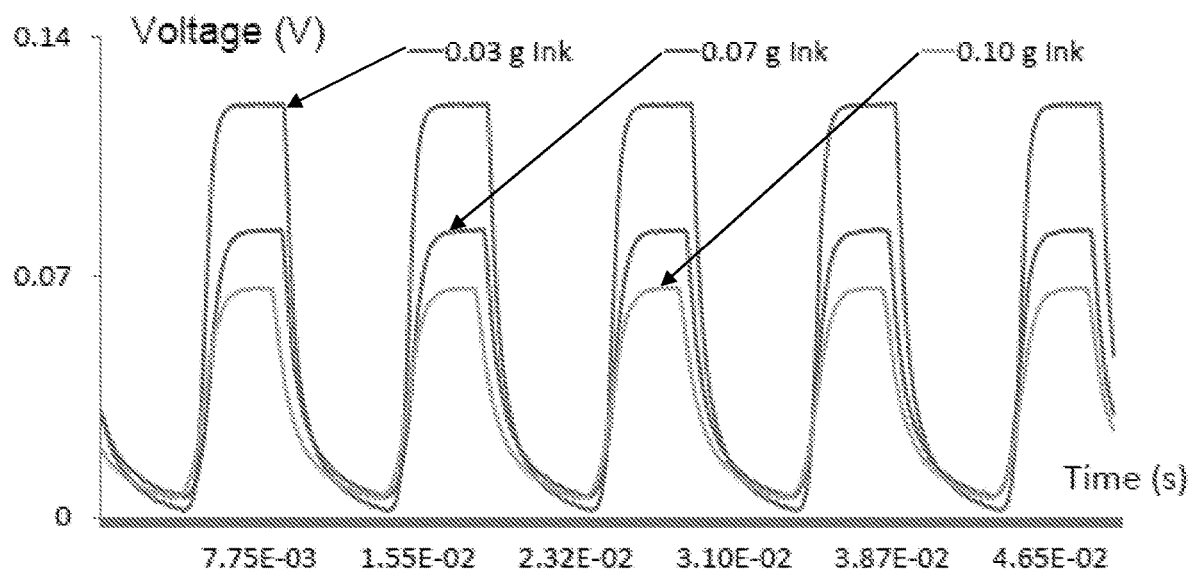
FIG. 18 shows a graph demonstrating voltage output of a photo detector for three different absorption conditions (0.03 g Ink, 0.07 g ink, and 0.10 g ink). Voltage (V) is shown on the y-axis and Time (s) is shown on the x-axis.

To test the effectiveness and sensitivity of the sensor under different absorption conditions, three different phantoms were prepared using the same amount of titanium dioxide powder and approximately 1×, 2× and 3× the amount of India ink established in Id., respectively. Once the phantoms were completely cured, a guide hole was defined with a drill in the middle of the phantom and the sensor can be inserted along with the glass tube sealed just in one end. FIG. 18 shows the output of the photodetector for each one of the phantoms under the same pulsed light exposure. The LED was be powered with a square wave of 100 Hz; the effect of the limited response time of the photodiode is shown in FIG. 18.

Figure 19:
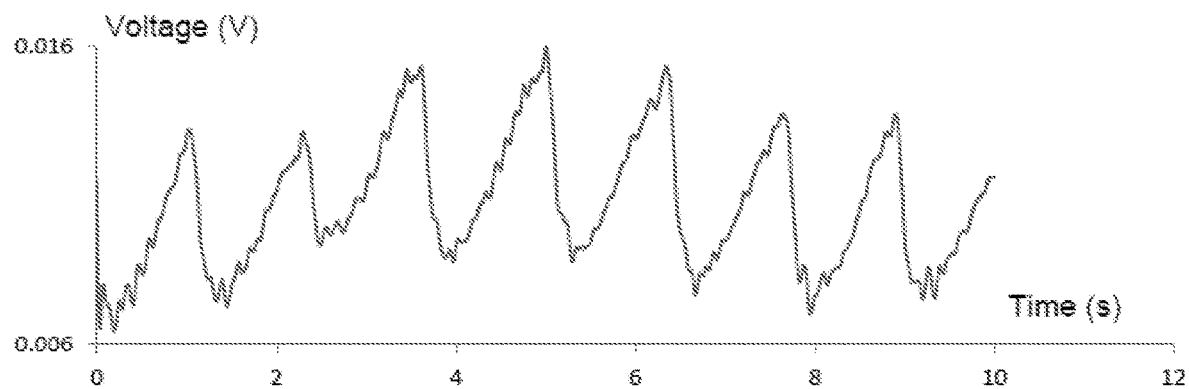
FIG. 19 shows a graph demonstrating a photoplethysmography (PPG) obtained from a subject via an injectable biophotonic sensor as described herein. Voltage (V) is shown on the y-axis and Time (s) is shown on the x-axis.

Finally, the PPG capability of the sensor was tested employing a setup similar to the one used in the previous experiment, but this time instead of placing the glass capsule inside the phantoms, it was placed between the thumb and index fingers of a human subject. The setup was shielded optically to prevent ambient light leakage. FIG. 19 shows the result of such a test which demonstrates a heartbeat related oscillation obtained after removing the DC component from the raw signal and applying a low-pass filter and moving average.

Figure 20:
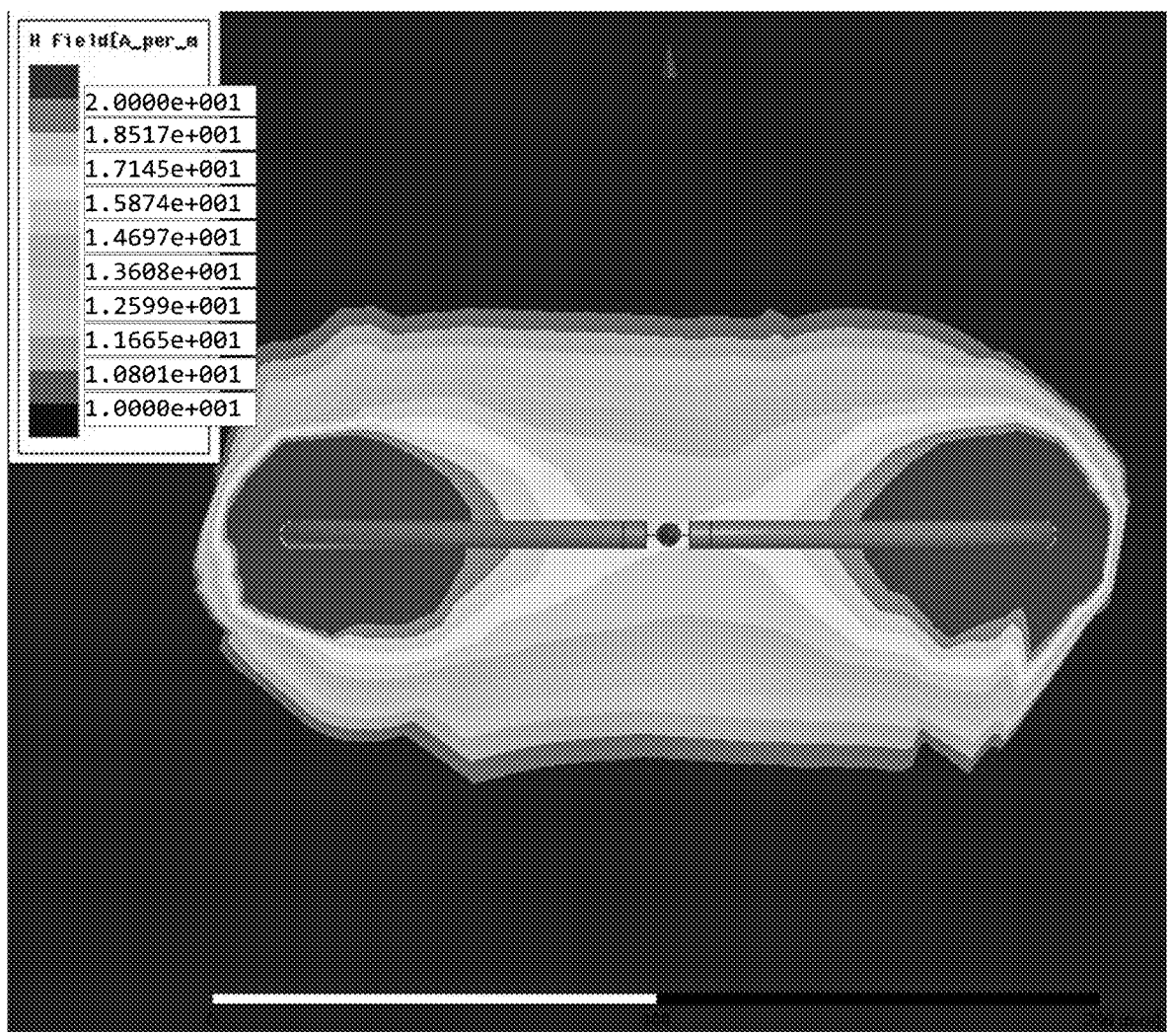
FIG. 20 shows an HFSS simulation plot of an induction coil when viewed from the top or the bottom demonstrating the distribution the magnetic field, where the red area represents a magnetic field strength that is above the exposure limit.
Figure 21:
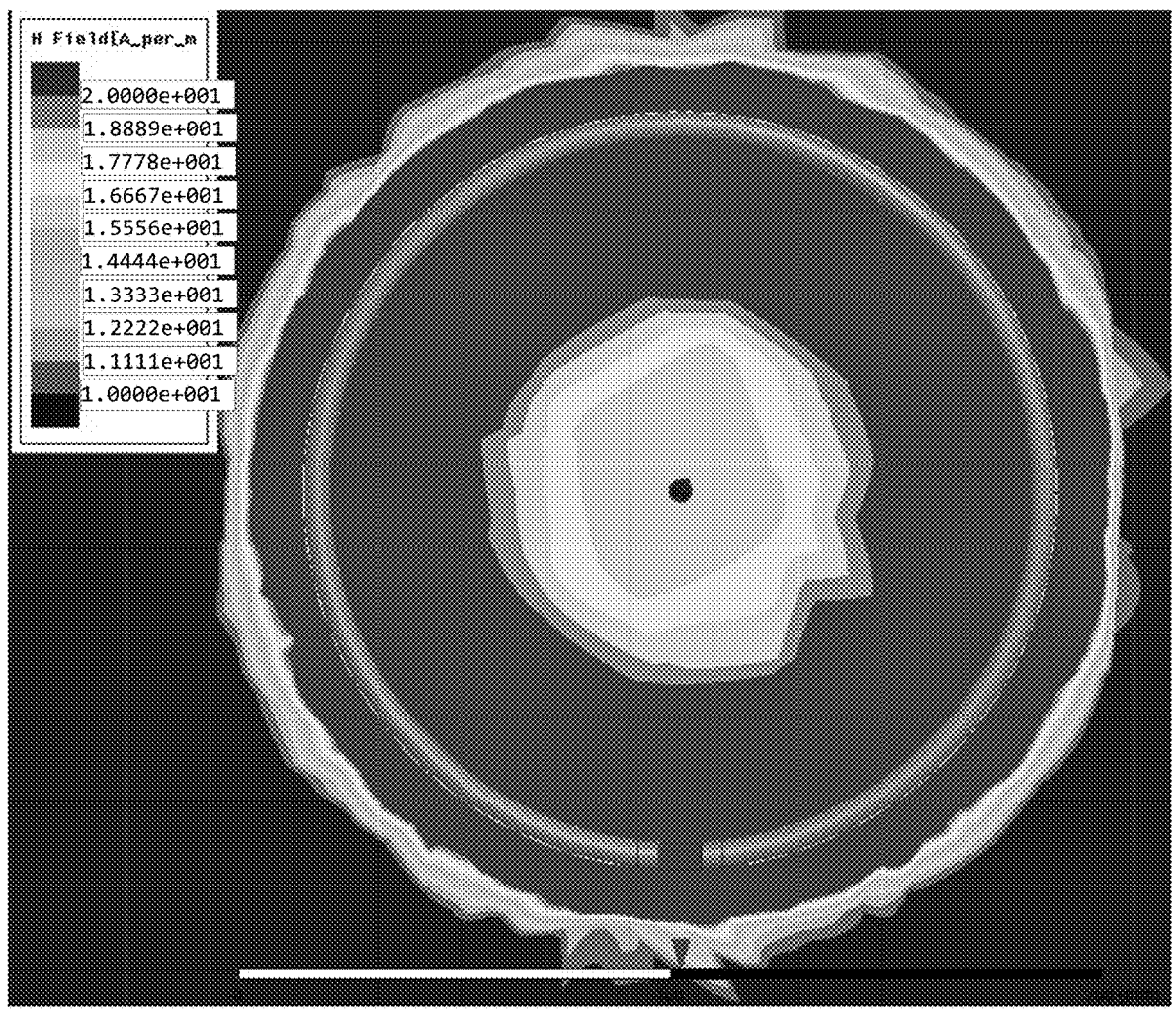
FIG. 21 shows an HFSS simulation plot of an induction coil when viewed from the side demonstrating the distribution the magnetic field, where the red area represents a magnetic field strength that is above the exposure limit.
Figure 22:
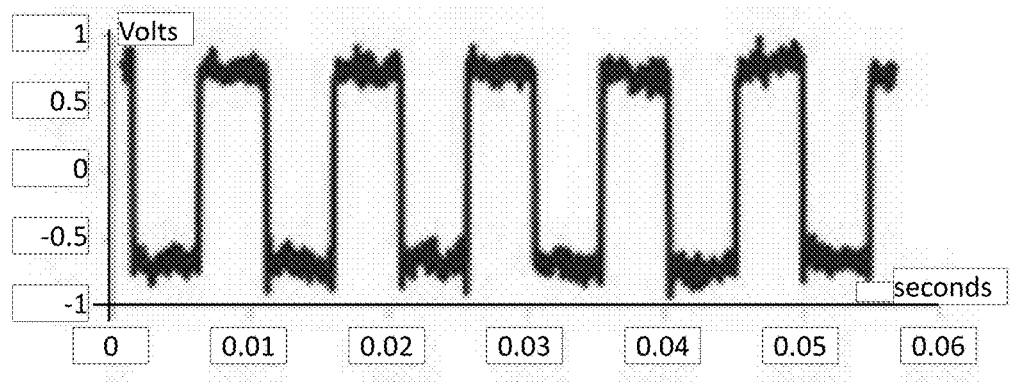
FIG. 22 shows a graph demonstrating a initialization and calibration pulse train programmed to the circuit within the capsule. Externally receiving this signal demonstrates that the capsule electronics is working correctly.
Figure 23:
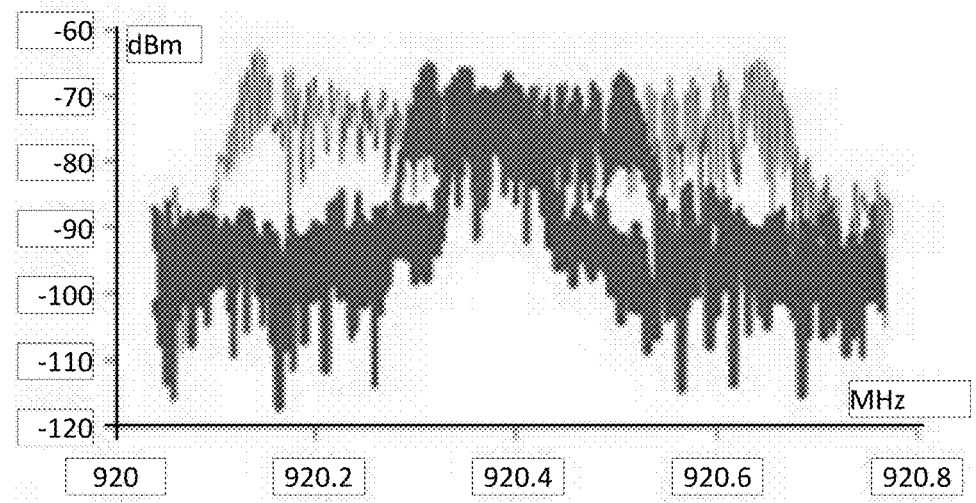
FIG. 23 shows a graph demonstrating the frequency spectrum of frequency modulated sine waves transmitted by the capsule prototype and received externally. The different colors refer to different signal amplitudes as also shown in in FIG. 24.
Figure 24:
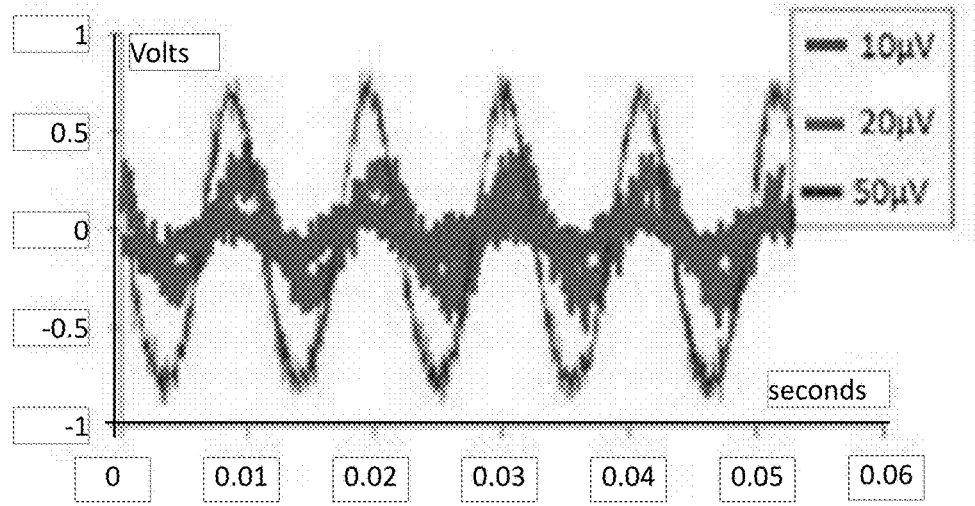
FIG. 24 shows a graph demonstrating three frequency modulated sine waves with different amplitudes transmitted by the capsule prototype and received externally. This indicates the amplification and transmission capability of the capsule.

To empirically determine power delivery below the exposure limit for magnetic field, the voltage on the LC-tank of the physical ZVS Flyback driver can be matched to its equivalent voltage in a simulation software (e.g., HSPICE from Synopsis, Inc.). This allowed for the determination of the current flowing through the loop antenna and was used in a finite element simulator (e.g., ANSYS HFSS from Ansoft Co.) to obtain the magnetic field distribution (see FIGS. 20-21).

In conclusion, in this Example, at least a glass and an epoxy encapsulated biophotonic sensors and their injection subcutaneously through a custom injector to perform photoplethysmographic measurements on animals is demonstrated. Two different experiments demonstrate at least the feasibility of the sensor under different absorption conditions and also its capability to monitor heartbeat related hemodynamic changes in a human subject. This Example also demonstrates the feasibility of using inductive coupling to power the system wirelessly, for which the light output from the capsule while being submerged in saline solution is tested.

Example 2

In Example 1, a subcutaneous capsule system is described for measuring HR, RR, SaO$_2$ by using biophotonic measurement. It is noteworthy that the motion artifact on these biophotonic measurements can be used to extract the actigraphy or motion activity of the animal. In this Example, this general physiological and activity monitoring of animals complemented by recording capability of biopotential activity of brain (EEG) or the muscle (EMG) to study certain conditions of the animals. For example, when injected into the scalp, measurement of HR, RR, SaO$_2$ and motion can be complemented by the biophotonic based cerebral oximetry and EEG based brainwave analysis to study the sleep and hibernation of animals. Alternatively, when injected into the muscle such a system can be used to study metabolism by measuring HR, RR, SaO$_2$, local/regional muscle oxygenation and oxygen consumption complemented by muscle potential and contraction analysis through EMG. Other suitable complementations will be appreciated by one of ordinary skill in the art in view of this disclosure and are within the scope and spirit of this disclosure. It is also noteworthy that these biopotential recordings can be fed into an adaptive filter to remove the motion induced artifacts from the signal.

The current "gold" standard approaches to measure EEG, ECG, EMG, HR, RR, $SaO_2$ and core body temperature (CBT) requires physical tethering of the animals to the recording apparatus with sensors either attached to the body externally or implanted surgically. Existing commercial wireless EEG or EMG systems are either too bulky or heavy causing mobility and behavioral disturbance related limitations. The need for replacing the battery may disturb the experiments. Recent developments in implantable systems for behavioral neuroscience studies require extensive surgeries for implantation. The Battery-Powered-BION (BPB) is the only system in the form factor of "injectable capsules" and offers muscle stimulation and its derivative IMES offers one channel EMG sensing capability for humans. These systems do not monitor key parameters such as HR, RR and $SaO_2$ and are not suitable for multichannel EEG recordings.

In this Example, the minimally invasive biophotonic capsule described in Example 1 is added with a wireless EEG or EMG recording device that can be injected subcutaneously under the scalp or muscle (FIGS. 3-4, 7, 12, and 13A-13E). As in Example 1, the miniaturized NIR light based oximetry system can be used to simultaneously detect multiple hemodynamic parameters (HR, RR, $SaO_2$ and motion) (FIG. 6). The miniature capsule can include extending EEG or EMG electrodes from two ends. A carefully designed injection mechanism (described in greater detail elsewhere herein) with 3D-printed injectors can avoid the buckling of the electrodes, which can be coated with a polymer or other coating (e.g. polyglycolic acid (PGA)) to temporarily enhance the structural rigidity. The capsule can also include a proportional to absolute temperature (PTAT) sensor for CBT. The system can be wirelessly powered through inductive coupling and transmit data back through telemetry methods such as frequency-shift-keying (FSK) modulated radio frequency (RF) field. This can eliminate the risk of behavioral disturbance caused by wires; remove the embedded batteries thereby miniaturizing the system even further; and prevent the need for changing batteries. The "subcutaneous" recording can improve the SNR thereby allowing for lower power consumption enabling wireless powering. This system is unique as no other existing system combine HR, RR, $SaO_2$, motion and EEG or EMG in injectable form factors.

Figure 9A:
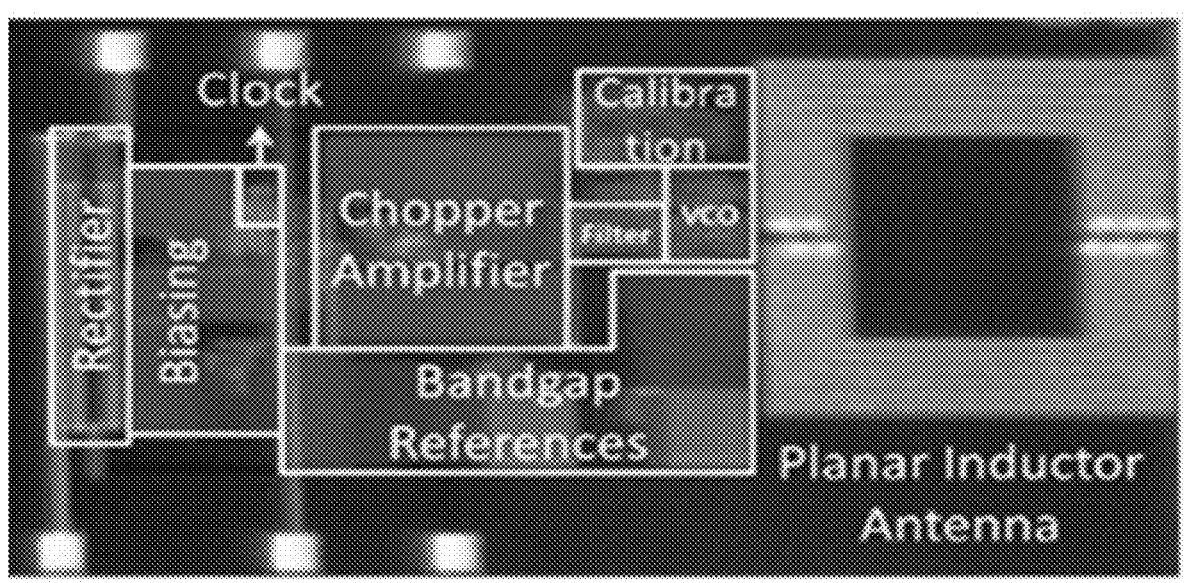
FIGS. 9A-9B shows an image demonstrating an embodiment injectable biophotonic sensor circuitry on a printed circuit board (PCB) (FIG. 9A) and circuit diagram (FIG. 9B).
Figure 9B:
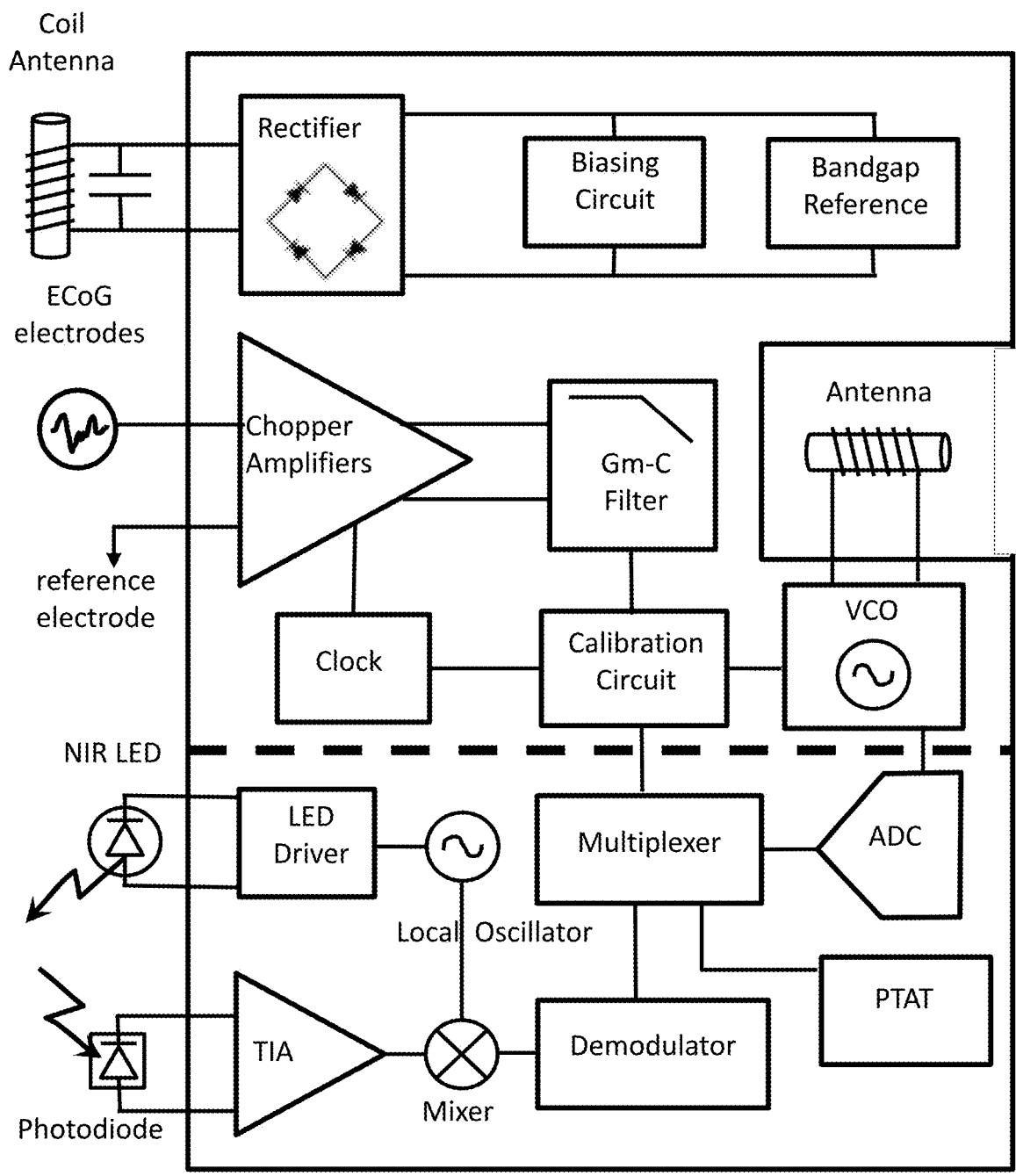
Figure 10:
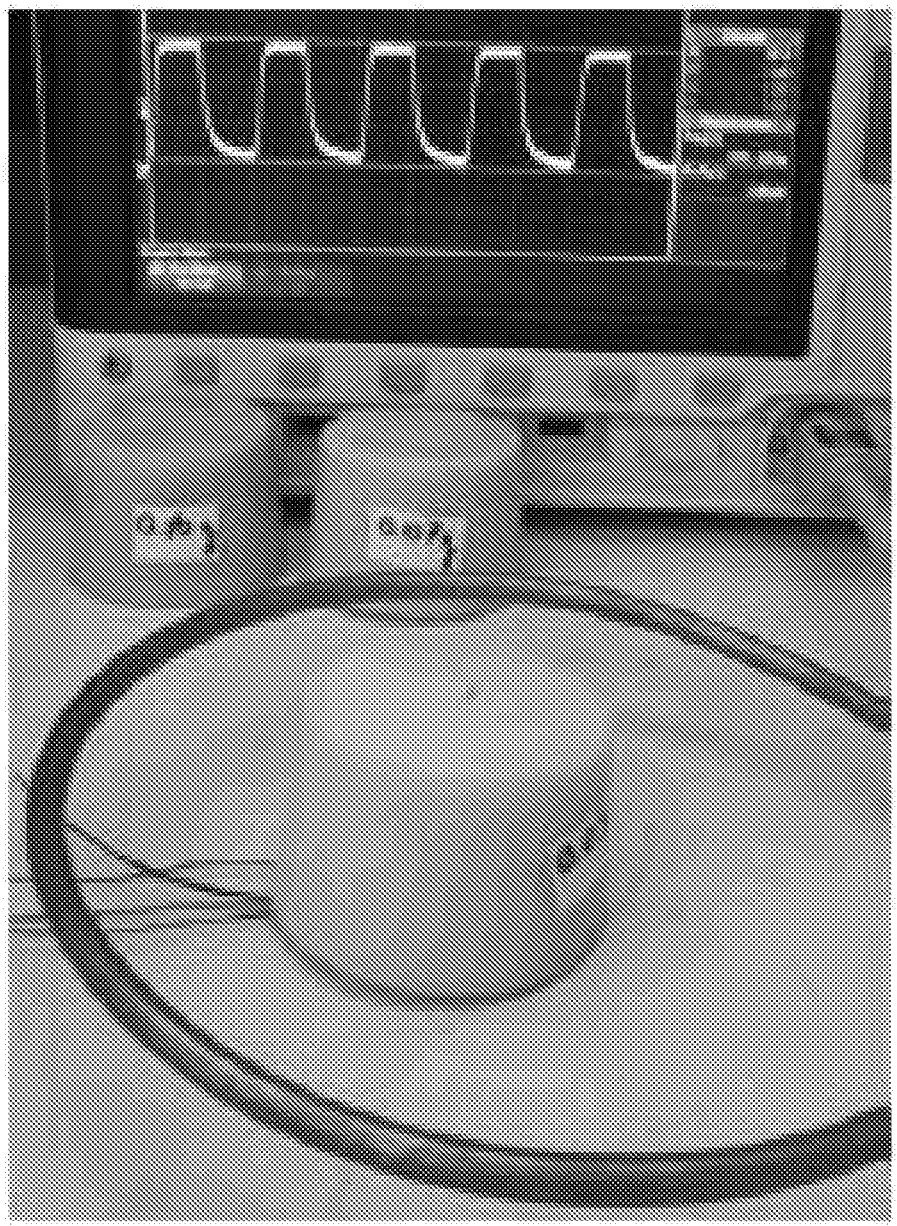
FIG. 10 shows an image demonstrating embodiments of an injectable biophotonic sensor and system as described herein.

To demonstrate this system, an inductively powered integrated circuit (e.g. an ASIC) can be added to the integrated circuit of Example 1 for wireless EEG/EMG recording capability (FIGS. 9A-9B). This integrated circuit can include seven blocks (FIGS. 9A-9B): low noise amplifiers (LNA), voltage controlled oscillators (VCO), full-wave rectifiers, filters, bandgap references, and a start-up test circuit. The start-up circuit can be configured to transmit a distinct square wave when the system is initially powered as a sign of successful connection and for calibrating signal amplitudes (see e.g. FIGS. 17 and 22-24). To eliminate 1/f noise, polarization voltage of electrodes, and coupling with power lines and power coil, a high CMRR chopper stabilized instrumentation amplifier can be AC coupled to the electrodes. These can use very low noise amplifiers, which was achieved by employing a Chopper amplifier consisting of an LNA in a feedback loop working at a frequency higher than the frequency of the signal to reduce the flicker noise at the output.

Figure 17:
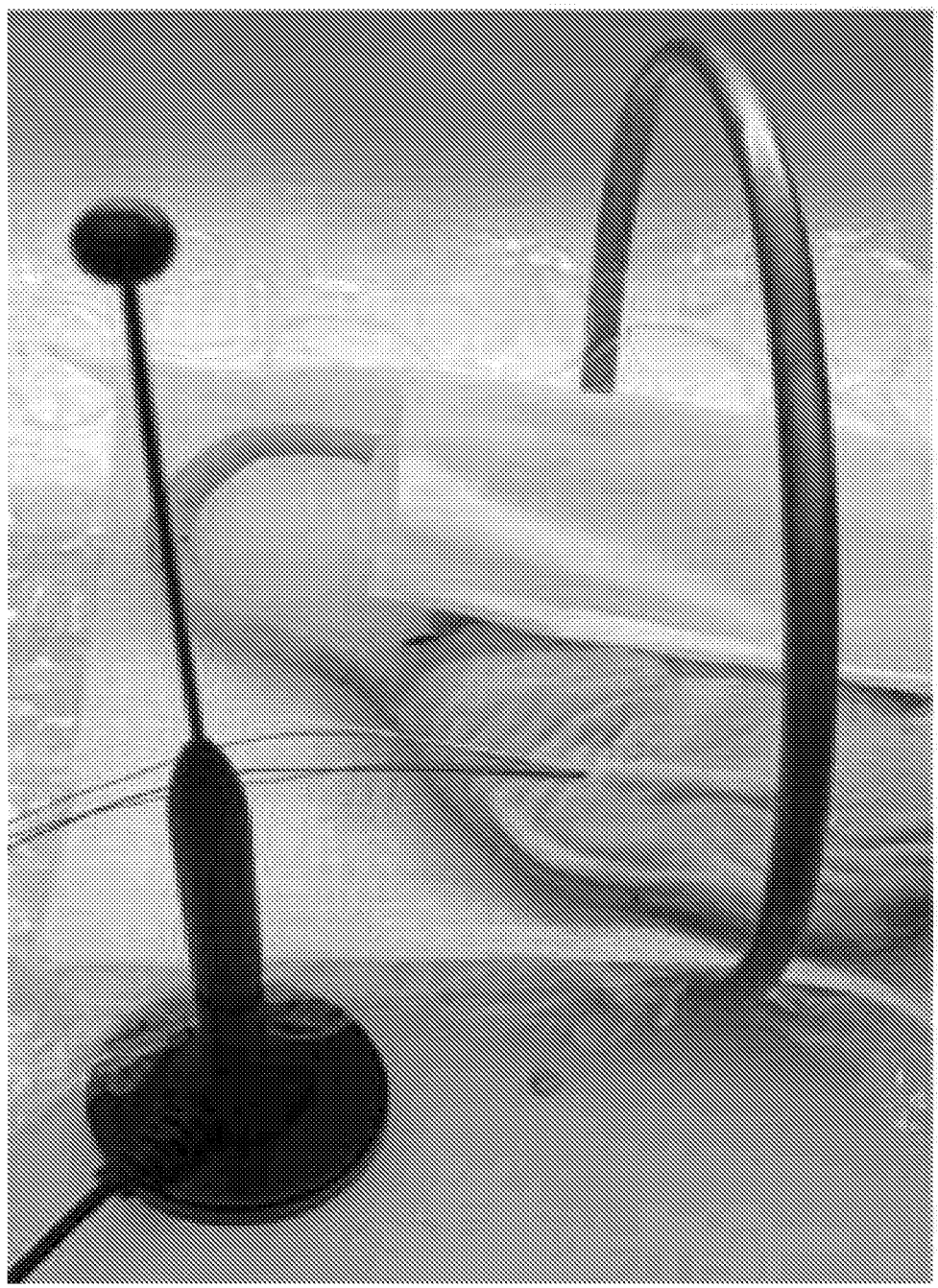
FIG. 17 shows an image demonstrating operation of an injectable biophotonic sensor and system as described herein after injection into a subject.

To eliminate the up converted noise of the Chopper amplifier and select the bandwidth of the signal, a low-pass Gm-C filter was be used. The outputs of the EEG and oximetry front-end circuits were multiplexed onto a single waveform and sampled at a rate of 5 kS/s by a 12-bit successive-approximation-register ADC. This TTL stream can modulate a freely running VCO outputting 5 dBm 6 MHz ISM band FSK signal into an on- or off-chip antenna (Harrison, R. R., Kier, R. J., Chestek, C. A., Gilja, V., Nuyujukian, P., Ryu, S., Shenoy, K. V. (2009). Wireless neural recording with single low-power integrated circuit, Neural Systems and Rehabilitation Engineering, IEEE Transactions on, 17(4), 322-329.) This antenna transferred the data to an external quarter-wave dipole antenna in the near field connected to a Bluetooth transceiver to wirelessly transmit the collected data to nearby data aggregator (FIG. 17).

The integrated circuit (e.g. ASIC) for wireless power/data transfer circuits is in the center of the system (FIGS. 9A-9B). The ASIC can be complemented by an externally connected LED-PD pair for oximetry, two to four 3 mil thick Pt/Ir wire (or microfabricated Parylene-C coated polyimide-Pt electrodes (Cheung, K. C. (2007). Implantable microscale neural interfaces. Biomedical microdevices, 9(6), 923-938 and Hassler, C., von Metzen, R. P., Ruther, P., & Stieglitz, T. (2010). Characterization of parylene C as an encapsulation material for implanted neural prostheses. Journal of Biomedical Materials Research Part B: Applied Biomaterials, 93(1), 266-274) for differential EEG/EMG and coil/wire antennas for wireless power and data transfer (FIG. 6). These can be interconnected on a microfabricated silicon PCB housing pads for lead-free soldering of external components. The integrated circuit (e.g. ASIC) can be wire-bonded to the PCB using ultrasonic wedge bonder. The wire (or microfabricated) electrodes can be directly connected to PCB for epoxy capsules or flip-chip bonded to through-glass-vias (TGV) (Hungar, K., & Mokwa, W. (2008). Gold/tin soldering of flexible silicon chips onto polymer tapes. Journal of Micromechanics and Microengineering, 18(6), 064002 and Topper, M., Klein, M., Buschick, K., Glaw, V., Orth, K., Ehrmann, Solzbacher, F. (2006, July). Biocompatible hybrid flip chip microsystem integration for next generation wireless neural interfaces. In IEEE Electronic Components and Technology Conference, 2006. Proceedings. 56th (pp. 705-708)) (FIG. 5).

Glass (e.g. bioglass) tubes can be used to build the capsule using commercially available laser sealing and cold welding techniques to attach circular glass wafer cut outs with incorporated through-glass-vias (TGV). Several TGV fabrication methods have been proposed before. Here, TGV can be obtained using plasma based deep reactive ion etching (DRIE) of glass and filling the through-holes with biocompatible electroplated gold over electroplated nickel (FIG. 5). Other suitable fabrication techniques and materials will be appreciated in view of this disclosure and are within the spirit and scope of this disclosure.

Figure 8:
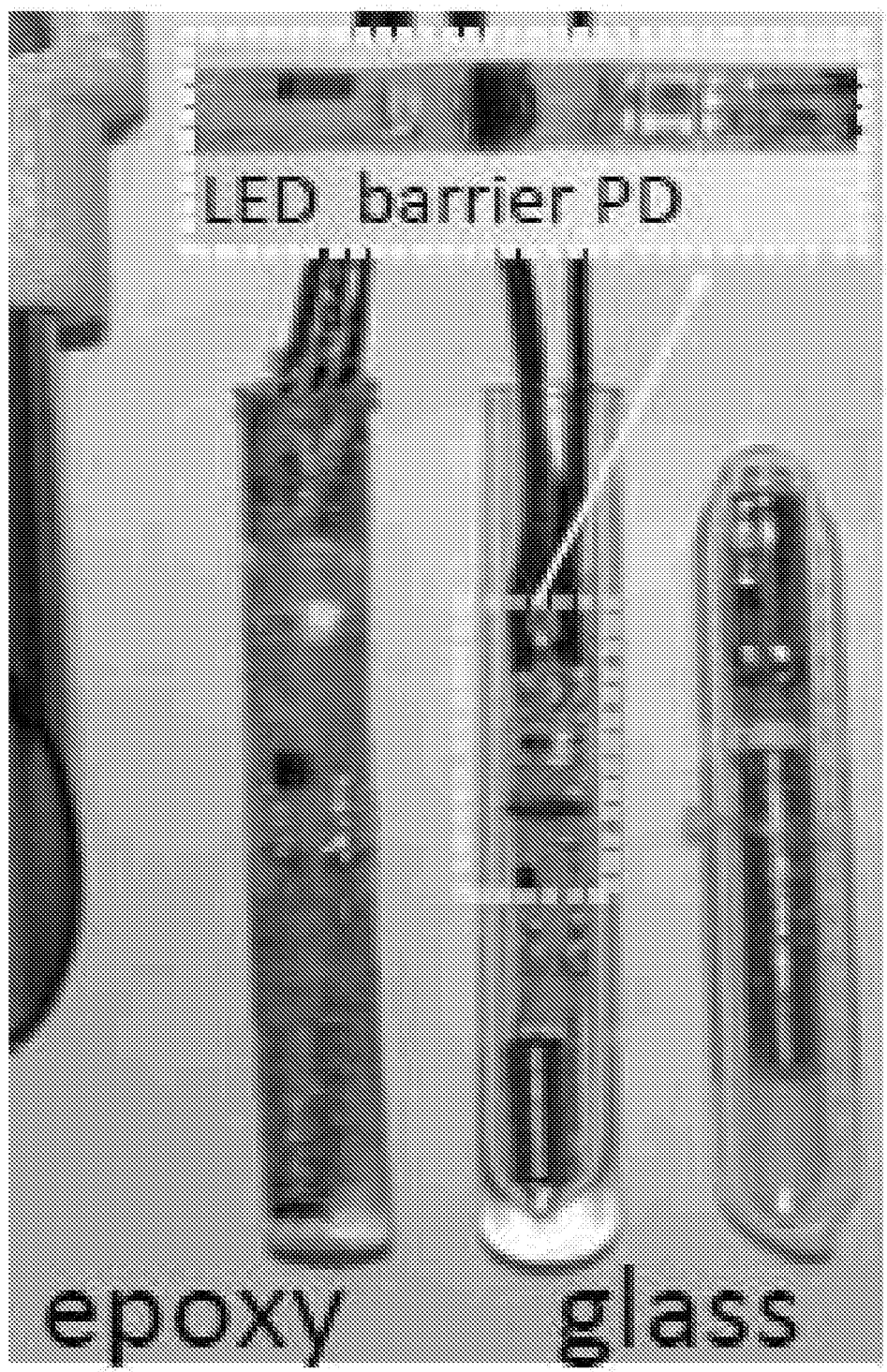
FIG. 8 shows images of injectable biophotonic sensors as described herein.

The glass capsules can be coated with a polymer and/or co-polymer (e.g. Parylene-C), which can be biocompatible and/or an anti-migratory material. To avoid buckling during the injection, the wire and microfabricated electrodes can be melt coated with a biodegradable polymer coating (e.g. PGA). PGA can provide a temporary and fast dissolving high rigidity structure for handling the softer electrodes, reducing the foreign body response and scar tissue formation. A wire antenna and the reference electrode can protrude from the scalp and stitched to the scalp where sharp tip of the reference is inserted to the back of the head (FIG. 6B). These are also useful to locate the devices and extract out with the injector if needed. The oximetry device can be standalone or can be combined with EEG/EMG (FIG. 6A). For subcutaneous injection, minimally-invasive mechanisms used for BION and canine microchip implant capsules can followed (FIGS. 7, 12, and 13A-13E) (Loeb, G. E., Peck, R. A., Moore, W. H., & Hood, K. (2001). BION™ system for distributed neural prosthetic interfaces. Medical engineering & physics, 23(1), 9-18). In addition to the glass, for shorter term applications polymer and/or co-polymer (e.g. Parylene-C) coated medical epoxy can be used to build the capsules, both with and without glass outside (FIGS. 5 and 8).

Other polymers can be used, that can, for example, improve the rigidity, during the injections can be shape memory polymers (Ware, T., Simon, D., Rennaker, R. L., & Voit, W. (2013). Smart Polymers for Neural Interfaces. Polymer Reviews, 53(1), 108-129 and Gilgunn, P. J., Khilwani, R., Kozai, T. D. Y., Weber, D. J., Cui, X. T., Erdos, G., Ozdoganlar, O. B., Fedder, G. K. (2012), an ultra-compliant, scalable neural probe with molded biodissolvable delivery vehicle. In IEEE 25th International Conference on Micro Electro Mechanical Systems (MEMS), 2012 (pp. 56-59) and/or fast dissolving carboxy-methyl cellulose. Porous polypropylene can be an alternative anti-migratory biocompatible polymer for Parylene-C. Parylene-C adheres to tissue and encapsulates but does not stick to glass allowing easy removal of the capsule with the injector or minor incision if an unexpected tissue reaction occurs. The capsules can be coated with a thin layer of dexamethasone loaded anti-inflammatory hydrogel or other anti-inflammatory compound.

Figure 16:
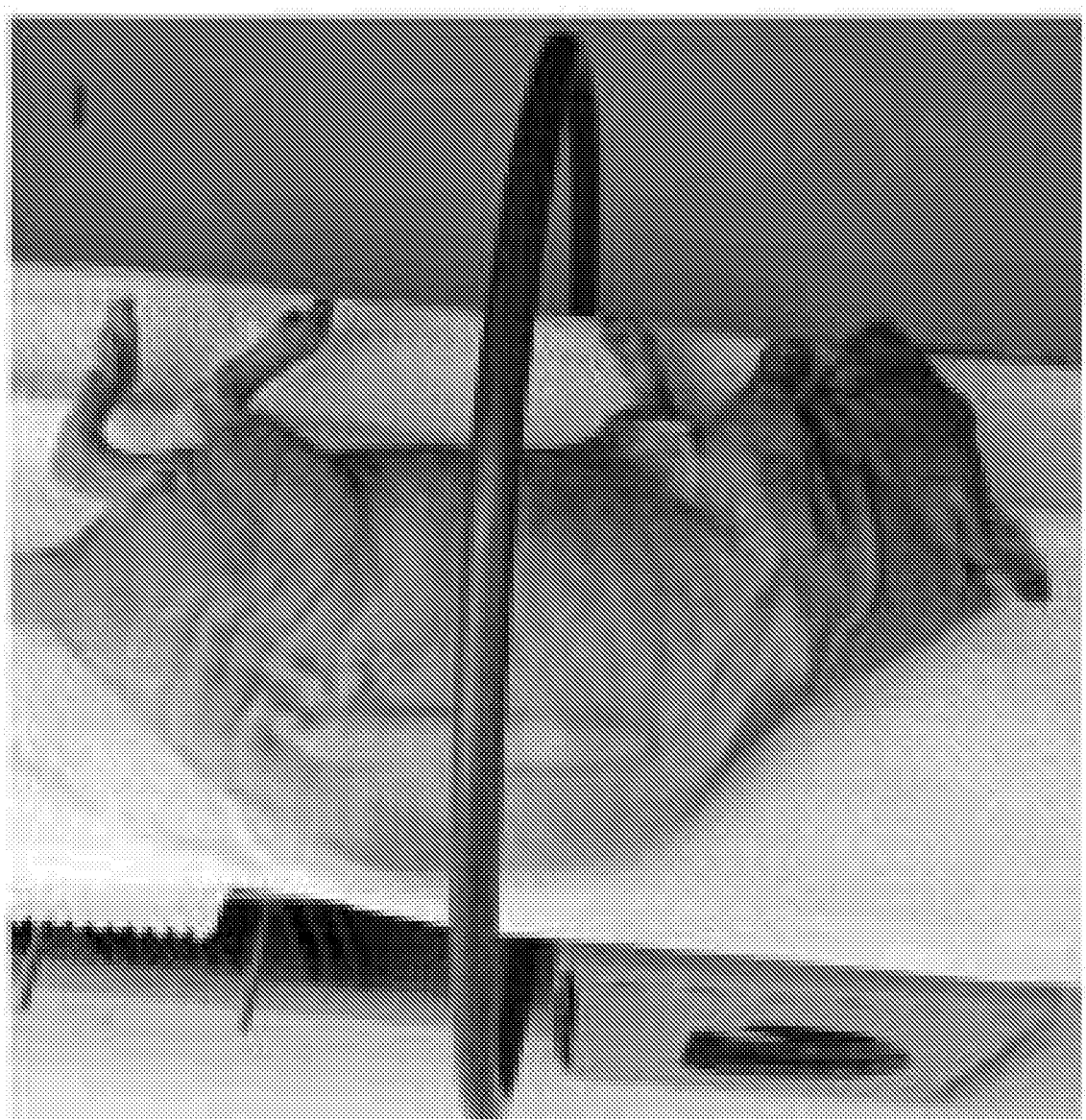
FIG. 16 shows an image demonstrating operation of an injectable biophotonic sensor and system as described herein after injection into a subject.

To demonstrate the functionality, the system was encapsulated in bioglass capsule and injected to a rat cadaver (FIGS. 16-17). The input channels were be connected to a function generator to apply sine waves at a set frequency and at different amplitudes. Any frequency in the physiologically relevant range (0.1 to 1,000,000 Hz) can be used here. For this demonstration, 1 KHz was chosen. A −70 dBm FM signal was received at a distance of 10 cm with a high gain whip receiving antenna connected to a network analyzer. An initial pulse train was also observed confirming a successful start-up. The feasibility of injection mechanism without buckling or crushing electrodes was also demonstrated with 3D printed plunger containing a hole to insert the electrodes while pushing the capsule in (FIG. 12).

Example 3

In this Example, animals with health problems were considered. Without limitation, these health problems can be cardiac, blood pressure, and/or diabetic related. These animals are either hospitalized or are taken care of at home environments. The traditional tape and bandage methods used in clinical environments to secure measurement devices to animals, such as pet dogs, cats, and horses, is both time consuming for researchers and uncomfortable for animals. Another major problem is that many of the methods used for measuring physiological responses involve restraint or handling, which can disturb and/or agitate the animal.

The biophotonic capsule in Example 1 can also be configured to work with externally injected functional materials such as polymers, which can change optical properties in the presence of certain interstitial conditions. For example, photons injected from the capsule can interact with such external polymers in the tissue (injected separately or as a part of the capsule). These polymers can change optical properties based on the glucose, oxygen, lactate and/or pH level of the tissue. This can be detected using the light detectors on the capsule and backscattering photons.

Alternatively, the biophotonic-biopotential capsule of Example 2 can be used for simultaneous performance of PPG and ECG. Beyond providing a more reliable heart rate information, the correlation of these two signals can be used to measure the pulse transit or pulse arrival time and thereby tracking the changes in blood pressure.

These systems could fill an important gap in small animal research and healthcare with subcutaneously-injected wirelessly-powered physiological sensors in a standard microchip implant form factor.

I claim:

1. A subcutaneously injectable biophotonic sensor comprising:
    a printed circuit board (PCB);
    a light source;
    a first optical sensing element;
    a light blocker located between the light source and the first optical sensing element;
    a second sensing element selected from the group consisting of: a temperature sensor, a microphone, an accelerometer, a biopotential electrode, a chemical sensor, a biochemical sensor, a biomolecule sensor, a pH sensor, an ion specific sensor, and any combination thereof;
    a receiver device configured to wirelessly receive power via inductive coupling from a transmitter device or a transmission coil, wherein the receiver device is selected from a wireless energy harvesting receiver device or a wireless energy harvesting receiver induction coil;
    a transparent outer casing,
    wherein the first sensing element, the second sensing element, and the receiver device are coupled to the PCB, wherein the first sensing element, the second sensing element, and the receiver device and the PCB are housed by the transparent outer casing, and wherein the light source is configured to emit photons directed through the transparent outer casing and wherein the first optical sensing element is configured to detect photons backscattered from tissue passing through the transparent outer casing; and
    wherein the injectable biophotonic sensor does not comprise a battery.

2. The injectable biophotonic sensor of claim 1, wherein the first sensing element is a light detector.

3. The injectable biophotonic sensor of claim 1, wherein the first sensing element and the second sensing element are each coupled to the outer casing.

4. The injectable biophotonic sensor of claim 1, wherein the first sensing element and the second sensing element are completely encapsulated by the outer casing.

5. The injectable biophotonic sensor of claim 1, wherein part of the first sensing element, part of the second sensing element, or parts of both the first sensing element and the second sensing element is integrated with the outer casing such that part of the first sensing element, part of the second sensing element, or parts of both the first sensing element and the second sensing element is exposed to an environment external to the outer casing.

6. The injectable biophotonic sensor of claim 1, wherein the receiver device is configured to wirelessly couple to the transmitter device or the transmission coil, and wherein the transmitter device or transmission coil is external to the outer casing.

7. The injectable biophotonic sensor of claim 6, wherein the transmitter device or the transmission coil is not coupled to the outer casing.

8. The injectable biophotonic sensor of claim 6, wherein the receiver device and PCB are completely contained within the outer casing.

9. The injectable biophotonic sensor of claim 1, further comprising a data transmitter coupled to the PCB, a data transmission antenna coupled to the PCB, or a receiving antenna coupled to the PCB.

10. The injectable biophotonic sensor of claim 1, wherein the sensor further comprises an electrode, wherein the electrode is coupled to the PCB board and is configured to detect a biopotential measurement in a subject.

11. The injectable biophotonic sensor of claim 1, wherein the second sensing element is configured to detect a biopotential measurement from a subject in which it is in injected.

12. The injectable biophotonic sensor of claim 1, wherein the PCB,
the first sensing element, the second sensing element, and the receiver device are physically coupled to the outer casing; and
further comprising a filling in voids encapsulated by the outer casing.

13. The injectable biophotonic sensor of claim 12, wherein the filling is a biocompatible or medical grade filling.

14. A system comprising:
an injectable subcutaneous capsule comprising a biophotonic sensor, wherein the biophotonic sensor comprises:
a printed circuit board (PCB);
a light source;
a first optical sensing element;
a light blocker located between the light source and the first optical sensing element;
a second sensing element, wherein the second sensing element is selected from the group consisting of: a temperature sensor, a microphone, an accelerometer, a biopotential electrode, a chemical sensor, a biochemical sensor, a biomolecule sensor, a pH sensor, an ion specific sensor, and any combination thereof;
a receiver device configured to wirelessly receive energy directly from a transmitter device or a transmission coil, wherein the receiver device is selected from a wireless energy receiver device or a wireless energy receiver induction coil;
a data transmitter, where the data transmitter is configured to transmit a signal through a data transmission antenna; and
a transparent outer casing,
wherein the first sensing element, the second sensing element, and the receiver device are coupled to the PCB;
wherein the first sensing element, the second sensing element, the receiver device, and the PCB are housed by the transparent outer casing;
wherein the light source is configured to emit photons through the transparent outer casing and wherein the first optical sensor is configured to detect photons backscattered from tissue passing through the transparent outer casing
wherein the injectable subcutaneous capsule does not comprise a battery;
a receiver, wherein the receiver is not coupled to the PCB, is external to the outer casing, and is configured to receive the signal transmitted by the data transmitter; and
a transmitter device or transmission coil, wherein the transmitter device or the transmission coil is not coupled to the PCB, is external to the outer casing, and is configured to wirelessly couple to the receiver device.

15. The system of claim 14, wherein the transmitter device or transmission coil is coupled to a collar, a bracelet, a vest, a shirt, pants, shoes, a wrap, a brace, or a bandage.

16. The system of claim 14, wherein the transmitter device or the transmission coil is coupled to a structure.

17. The system of claim 14, wherein the receiver device and transmitter device or the receiver device and the transmission coil are configured to wirelessly transmit energy from the transmitter device or the transmission coil to the receiver device when the receiver device is within responsive proximity with the transmitter device or the transmission coil.

18. The system of claim 14, wherein the system further comprises a power source, where the power source is coupled to the transmitter device or the transmission coil.

19. The system of claim 14, wherein the system further comprises a data storage device, where the data storage device is configured to receive the signal transmitted from the data transmission antenna.

20. The system of claim 19, wherein the system further comprises a processor, where the processor is in communication with the biophotonic sensor, the data storage device, or both.

21. The system of claim 14, wherein the second sensing element is configured to detect a biopotential measurement from a subject in which it is in injected.

22. A method comprising:
injecting an injectable biophotonic sensor subcutaneously into a subject;
directing photons emitted from a light source through a transparent outer casing at the subject's tissue;
blocking photons directly emitted from the light source using a light blocker located between the light source and a first optical sensing element;
detecting photons with the first optical sensing element, where the photons are backscattered from the tissue then pass through the transparent outer casing;
receiving energy wirelessly, via a receiver device configured to wirelessly receive energy or a receiver induction coil configured to wirelessly receive energy, from a transmitter; and
detecting a biopotential measurement from the subject with a second sensing element, wherein the second sensing element is selected from the group consisting of: a temperature sensor, a microphone, an accelerometer, a biopotential electrode, a chemical sensor, a biochemical sensor, a biomolecule sensor, a pH sensor, an ion specific sensor, and any combination thereof;
wherein the first sensing element, a second sensing element, and the receiver device or the receiver induction coil are coupled to a printed circuit board (PCB).

23. The method of claim 22, further comprising the step of detecting a physiologic parameter of the subject by the injectable biophotonic sensor.

24. The method of claim 23, wherein the step of detecting physiologic parameter of the subject by the injectable biophotonic sensor is the detection of a heart rate (HR), heart rate variability (HRV), respiratory rate (RR), arterial oxygen saturation (SaO$_2$), or motion from a biophotonic measurement.

25. The method of claim 24, further comprising detecting a biopotential measurement of the subject by the injectable biophotonic sensor, wherein the biopotential measurement is related to electroencephalography (EEG), electrocardiography (ECG), electromyography (EMG), or electrooculography (EOG).

26. The method of claim 25, further comprising recording the biophotonic measurement and the biopotential measurement to calculate a pulse transit time or pulse arrival time of the subject, wherein the biopotential measurement is ECG and the biophotonic measurement is photoplethysmogram.

27. The method of claim 24, wherein the motion is related to contraction of the heart of the subject, movement of the subject, or respiration of the subject.

* * * * *